US007994219B2

(12) United States Patent  
Serhan et al.

(10) Patent No.: US 7,994,219 B2  
(45) Date of Patent: Aug. 9, 2011

(54) APPROACH TO ANTI-MICROBIAL HOST DEFENSE WITH MOLECULAR SHIELDS WITH LIPOXIN COMPOUNDS

(75) Inventors: Charles N. Serhan, Needham, MA (US); Sean P. Colgan, North Reading, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 892 days.

(21) Appl. No.: 11/837,693

(22) Filed: Aug. 13, 2007

(65) Prior Publication Data

US 2008/0214665 A1    Sep. 4, 2008

Related U.S. Application Data

(63) Continuation of application No. 10/323,591, filed on Dec. 18, 2002.

(60) Provisional application No. 60/342,138, filed on Dec. 18, 2001.

(51) Int. Cl.
| | |
|---|---|
| *A01N 37/00* | (2006.01) |
| *A01N 37/02* | (2006.01) |
| *A61K 31/215* | (2006.01) |
| *A61K 31/22* | (2006.01) |
| *A61K 31/23* | (2006.01) |

(52) U.S. Cl. .......................... 514/552; 514/529; 514/546

(58) Field of Classification Search .................. 514/529, 514/546, 552

See application file for complete search history.

(56) References Cited

U.S. PATENT DOCUMENTS

| | | | |
|---|---|---|---|
| 4,560,514 | A | 12/1985 | Samuelsson et al. |
| 4,576,758 | A | 3/1986 | Morris |
| 4,780,281 | A | 10/1988 | Marnett et al. |
| 5,049,681 | A | 9/1991 | Sato |
| 5,079,261 | A | 1/1992 | Serhan et al. |
| 5,322,699 | A | 6/1994 | Wright et al. |
| 5,441,951 | A | 8/1995 | Serhan |
| 5,648,512 | A | 7/1997 | Serhan |
| 5,650,435 | A | 7/1997 | Madara et al. |
| 5,998,487 | A | 12/1999 | Brahms et al. |
| 6,329,425 | B1 | 12/2001 | Madara et al. |

FOREIGN PATENT DOCUMENTS

| | | |
|---|---|---|
| JP | 62-198677 | 9/1987 |
| JP | 63-88153 | 4/1988 |
| JP | 1-228994 | 9/1989 |
| JP | 3-227922 | 10/1991 |
| WO | WO 94/29262 | 12/1994 |
| WO | WO 95/01179 | 1/1995 |
| WO | WO 98/11049 | 3/1998 |
| WO | WO 00/13685 | 3/2000 |
| WO | WO 00/54767 | 9/2000 |
| WO | WO 00/55109 | 9/2000 |
| WO | WO 01/60778 | 8/2001 |
| WO | WO 01/70664 | 9/2001 |
| WO | WO 03/039533 | 5/2003 |
| WO | WO 03/051350 | 6/2003 |

OTHER PUBLICATIONS

Corey, et al., "On the Synthesis and Structure of Lipoxin B", Tetrahedron Letters, vol. 26, No. 16, (1985) pp. 1919-1922.
Takano, et al., "Neutrophil-mediated Changes in Vascular Permeability Are Inhibited by Topical Application of Aspiring-triggered 15-epi-lipoxin A4 and Novel Lipoxin B4", J. Clin. Invest. The American Society for Clinical Investigations, Inc., vol. 101, No. 4, 1998, pp. 819-826.
Nguyen, et al. "Nonsteroidal anti-inflammatory drug use in dentistry: Gastrointestinal Implications", Pharmacology, Nov. 1999, pp. 590-596.
Maddox, et al., "Lipoxin B4 Regulates Human Monocyte/Neutrophil Adherence and Motility: Design of Stable Lipoxin B4 Analogs with Increased Biologic Activity", The FASEB Journal, vol. 12, Apr. 1998, pp. 487-494.
Pouliot M., et al, "Lipoxin A4 and Aspirin-Triggered 15-EPI-LXA4 Inhibit Tumor Necrosis factor-1 Alpha-Initiated Neutrophil Responses and Trafficking: Novel Regulators of a Cytokine-Chemokine Axis Relevant to Periodontal Diseases", Journal of Periodontal Research, vol. 34, No. 7, Oct. 1999, pp. 370-373.
Fiore et al., "Lipoxin Recognition Sites", *The Journal of Biological Chemistry*, vol. 267, No. 23, 1992, pp. 16168-16176.
Claria, J. et al., Aspirin Triggers Previously Undescribed Bioactive Eicosanoids by Human Endothelial Cell-Leukocyte Interactions:, *Proc, Nat'l Acad. Sci.*, vol. 92, 1995, pp. 9475-9479.
Serhan, "Lipoxins: Eicosanoids Carrying Intra- and Intercellular Messages", *Journal of Bioenergetics and Biomembranes*, vol. 23, No. 1, 1991, pp. 105-122.
Mizukami, et al., "ω-Hydroxylation of Lipoxin $B_4$ by Human Neutrophil Microsomes: Identification of ω-Hydroxy Metabolite of Lipoxin $B_4$ and Catalysis by Leukotriene $B_4$ ω-Hydroxylase (cytochrome P-450LTBω)", *Biochimica et Biophysica Acta*, No. 1168, 1993, pp. 87-93.
Popov, et al., "Effect of Lipoxin B on Colony-Forming Ability of Human Peripheral Blood Mononuclears in a Diffusion Chamber", Translated from *Byulleten' Eksperimental' noi Biologii i Meditsiny*, vol. 107, No. 1, 1989, pp. 80-83.
Katoh, et al., "Renal Hemodynamic Actions of Lipoxin in Rats: A Comparative Physiological Study", American Journal Physiology, vol. 263, 1992, pp. F436-F442.
Nigam, et al., "Lipoxin $A_4$ and Lipoxin $B_4$ Stimulate the Release but not the Oxygenation of Arachidonic Acid in Human Neutrophils: Dissociation between Lipid Remodeling and Adhesion", *Journal of Cellular Physiology*, Vo. 142, 1990, pp. 512-523.
Lee, et al., "Inhibition of Leukotriene $B_4$-Induced Neutrophil Migration by Lipoxin $A_4$: Structure-Function Relationships", *Biochemical and Biophysical Research Communications*, vol. 180, No. 3, 1991, pp. 1416-1421.
Nicolaou, et al., "Lipoxins and Related Eicosanoids: Biosynthesis, Biological Properties, and Chemical Synthesis", *Angew. Chem. Int. Ed. Engl.*, vol. 30, 1991, pp. 1100-1116.
Nicolaou, et al., "Total Synthesis of Novel Geometric Isomers of Lipoxin $A_4$ and Lipoxin $B_4$", Reprint from *The Journal of Organic Chemistry*, vol. 54, No. 23, 1989, pp. 5527-5535.
Brady, et al., "Leukotrienes Stimulate Neutrophil Adhesion to Mesangial Cells: Modulation with Lipoxins", *American Journal Physiology*, vol. 259, 1990, pp. F809-F815.

(Continued)

*Primary Examiner* — Yong S. Chong  
(74) *Attorney, Agent, or Firm* — Colin L. Fairman; Scott D. Rothenberger; Fulbright & Jaworski

(57) ABSTRACT

Methods to cause tissue, such as mucosal cells, to express increased amounts of bactericidal permeability increasing protein (BPI) are described. The BPI inducing agents include, for example, lipoxin compounds.

4 Claims, 9 Drawing Sheets

OTHER PUBLICATIONS

Nicolaou et al., "Identification of a novel 7-*cis*-11-*trans*-lipoxin $A_4$ generated by human neutrophils: total synthesis, spasmogenic activities and comparison with other geometric isomers of lipoxins $A_4$ and $B_4$", *Biochimica et Biophsica Acta*, 1003, 1989, pp. 44-53.

Serhan et al., "Design of Lipoxin A4 Stable Analogs That Block Transmigration and Adhesion of Human Neutrophils", *Biochemistry*, vol. 34, No. 44, 1995, pp. 14609-14615.

Maddox, et al., "Lipoxin A4 Stable Analogs Are Potent Mimetics That Stimulate Human Monocytes and THP-1 Cells via a G-protein-linked Lipoxin A4 Receptor", *The Journal of Biological Chemistry*, vol. 272, No. 11, 1997, pp. 6972-6978.

Claria, J. "Aspirin-Triggered Lipoxins (15-epi-LX) Are Generated by the Human Lung Adenocarcinoma Cell Line (A549)- Neutrophil Interactions and Are Potent Inhibitors of Cell Proliferation", *Molecular Medicine*, vol. 2, No. 5, Sep. 1996, pp. 583-596.

Badr, K.F. "15-Lipoxygenase Products as Leukotriene Antagonists: Therapeutic Potential in Glomerulonephritis", *Kidney International*, vol. 42, Supp. 38, 1992, pp. S101-S108.

Dahlen, S.E. "Lipoxins and other Lipoxygenase Products with Relevance to Inflammatory Reactions in the Lung", *Annals of the New York Academy of Sciences*, Advances in the Understanding and Treatment of Astham, (no date available), pp. 262-273.

Fiore, S. "The Lipoxin Biosynthetic Circuit and their Actions with Human Neutrophils", *Advances in Experimental Medicine and Biology*, vol. 314, 1991, pp. 109-132.

Fiore, S, et al. "Induction of Functional Lipoxin A4 Receptors in HL-60 Cells", *Blood*, vol. 81, No. 12, 1993, pp. 3395-3403.

Lederman, S. et al. "Identification of a Novel Surface Protein on Activated CD4+ T Cells that Induces Contact-Dependent B Cell Differentiation (Help)", *J. Exp. Med.*, vol. 175, 1992, pp. 1091-1101.

Madara, J.L. et al. "A Simple Approach to Measurement of Electrical Parameters of Cultured Epithelial Monolayers: Use in Assessing Neutrophil-Epithelial Interactions", *J. Tiss. Cult. Meth.*, vol. 14, 1992, pp. 209-216.

Madara, J.L. et al. "5'-Adenosine Monophosphate is the Neutrophil-derived Paracrine Factor that Elicits Chloride Secretion from T84 Intestinal Epithelial Cell Monolayers", *J. Clin. Invest.*, vol. 91, 1993, pp. 2320-2325.

Nash, S. et al. "Effects of Polymorphonuclear Leukocyte Transmigration on the Barrier Function of Cultured Intestinal Epithelial Monolayers", *J. Clin. Invest.*, vol. 80, 1987, pp. 1104-1113.

Noelle, R.J. et al., "A 39-kDa Protein on Activated Helper T Cells Binds CD40 and Transduces the Signal for Cognate Activation of B Cells ", *Proc. Natl. Acad. Sci. USA*, vol. 89, 1992, pp. 6550-6554.

Parkos, C.A. et al. "Neutrophil Migration Across a Cultured Intestinal Epithelium", *J. Clin. Invest.*, vol. 88, 1991, pp. 1605-1612.

Parkos, C.A. et al. "Neutrophil Migration Across a Cultured Epithelial Monolayer Elicits a Biphasic Resistance Response Representing Sequential Effects on Transcellular and Paracellular Pathways", *The Journal of Cell Biology*, vol. 117, No. 4, 1992, pp. 757-764.

Pettitt, T.R. et al., "Synthesis of Lipoxins and Other Lipoxygenase Products by Macrophages form the Rainbow Trout, Oncorhynchus Mykiss", *The Journal of Biological Chemistry*, vol. 266, No. 14, 1991, pp. 8720-8726.

Samuelsson, B., "An Elucidation of the Arachidonic Acid Cascade Discovery of prostaglandins, Thromboxane and Leukotrienes", *Drugs*, vol. 33, Supp. 1, 1987, pp. 209.

Leff, A.R. "Role of Leukotrienes in Bronchial Hyperresponsiveness and Cellular Responses in Airways", *Amer. Journal of Respiratory and Critical Care Medicine*, vol. 161, 2000, pp. S125-S132.

Bousquet, J. et al. "Asthma. From bronchoconstriction to Airways Inflammation and Remodeling", *Amer. Journal of Respiratory and Critical Care Medicine*, vol. 161, 2000, pp. 1720-1745.

Robinson, D.S. et al. "Predominant TH2-like Bronchoalveolar T-lymphocyte Population in Atopic Asthma", *New England Journal of Medicine*, vol. 326, 1992, pp. 298-304.

Broide, D.H. et al. "Cytokines in Symptomatic Asthma Airways", *J. Allergy Clin. Immunol.*, vol. 89, 1992, pp. 958-967.

Samuelsson, B. "From Studies of Biochemical Mechanisms to Novel Biological Mediators: Prostaglandin Endoperoxides, Thromboxanes and Leukotrienes", *In Les Prix Nobel: Nobel Prizes, Presentations, Biographies and Lectures*, 1982, pp. 153-174.

Drazen, J.M. et al. "Treatment of Asthma with Drugs Modifying the Leukotriene Pathway", *New England Journal of Medicine*, vol. 340, 1999, pp. 197-206.

Serhan, C.N. et al. "Lipid Mediator Networks in Cell Signaling: Update and Impact of Cytokines", *FASEB Journal*, vol. 10, 1996, pp. 1147-1158.

McMahon, B. et al. "Lipoxins: Revelations on Resolution", *Trends in Pharmacological Sciences*, vol. 22, 2001, pp. 391-395.

Levy, B.D. et al. "Lipid Mediator Class Switching During Acute Inflammation: Signals in Resolution", *Nature Immunology*, vol. 2, 2001, pp. 612-619.

Lee, T.H. et al. "Identification of Lipoxin A4 and its Relationship to Sulfidopeptide Leukotrienes C4, D4, and E4 in the Bronchoalveolar Lavage Fluids obtained from patients with Selected Pulmonary Diseases", *Amer. Review of Respiratory Disease*, vol. 141, 1990, pp. 1453-1458.

Badr, K.F. et al., "Lipoxin A4 Antagonizes Cellular and in Vivo Actions of Leukotriene D4 in rat glomerular mesangial cells: Evidence for Competition at a Common Receptor", *Proc. Nat'l. Acad. Sci. USA*, vol. 86, 1989, pp. 3438-3442.

Gronert, K. et al. "Selectivity of Recombinant Human Leukotriene D4 Leukotriene B4 and Lipoxin A4 Receptors with Aspirin- Triggered 15-epi-LXA4 and Regulation of Vascular and Inflammatory Responses", *Amer. J. Path*, vol. 158, 2001, pp. 3-9.

Takano, T. et al. "Aspirin-Triggered 15-epi-lipoxin A4 (LXA4) and LXA4 Stable Analogues are Potent Inhibitor of Acute Inflammation: Evidence for Anti-Inflammatory Receptors", *Journal of Experimental Medicine*, vol. 185, 1997, pp. 1693-1704.

De Sanctis, G.T. et al. "Interleukin-8 Receptor Modulates IgE Production and B-cell Expansion and Trafficking in Allergen-Induced Pulmonary Inflammation", *J. Clin. Invest.*, vol. 103, 1999, pp. 507-515.

De Sanctis, G.T. et al. "Contribution of Nitric Oxide Synthases 1, 2, and 3 to Airway Hyperresponsiveness and Inflammation in a Murine Model of Asthma", *Journal of Experimental Medicine*, vol. 189, 1999, pp. 1621-1630.

Clish, C.B. et al. "Local and Systemic Delivery of a Stable Aspirin-Triggered Lipoxin Prevents Neutrophil Recruitment in Vivo", *Proc. Nat'l. Acad. Sci. USA*, vol. 96, 1999, pp. 8247-8452.

Holgate, S.T. "The Epidemic of Allergy and Asthma", *Nature*, vol. 402, 1999, pp. B2-B4.

Drazen, J.M. et al. "Heterogeneity of Therapeutic Responses in Asthma", *British Medical Bulletin*, vol. 56, 2000, pp. 1054-1070.

Bryan, S.A. et al. "Effects of Recombinant Human Interleukin-12 on Eosinophils, Airway Hyper-Responsiveness, and the late Asthmatic Response", *Lancet*, vol. 356, 2000, pp. 2149-2153.

Leckie, M.J. et al. "Effects of an Interleukin-5 Blocking Monoclonal Antibody on Eosinophils, Airway Hyper-Responsiveness, and the late Asthmatic Response", *Lancet*, vol. 356, 2000, pp. 2144-2148.

Christie, P.E. et al. "The Effects of Lipoxin A4 on Airway Responses in Asthmatic Subjects", *Amer. Review of Respiratory Disease*, vol. 145, 1992, pp. 1281-1284.

Dahlen, S.E. et al. "Actions of Lipoxin A4 and Related Compounds in Smooth Muscle Preparations and on the Microcirculation in Vivo", *Advances in Experimental Medicine & Biology*, vol. 229, 1988, pp. 107-130.

Venkayya, R. et al. "The Th2 Lymphocyte Products IL-4 and IL-13 Rapidly Induce Airway Hyperresponsiveness Through Direct Effects on Resident Airway Cells", *Amer. Journal of Respiratory Cell & Molecular Biology*, vol. 26, 2002, pp. 202-208.

Laporte, J.C. et al. "Direct Effects of Interleukin-13 on Signaling Pathways for Physiological Responses in Cultured Human Airway Smooth Muscle Cells", *Amer. Journal of Respiratory & Critical Care Medicine*, vol. 164, 2001, pp. 141-148.

Cowburn, A.S. et al. "IL-5 Increases Expression of 5-Lipoxygenase-activating Protein and Translocates 5-Lipoxygenase to the Nucleus in Human Blood Eosinophils", *J. Immun.*, vol. 163, 1999, pp. 456-465.

Hisada, T. et al. "Cysteinyl-leukotrienes Partly Mediate Eotaxin-Induced Bronchial Hyperresponsiveness and Eosinophilia in IL-5 Transgenic Mice", *Amer. Journal of Respiratory & Critical Care Medicine*, vol. 160, 1999, pp. 571-575.

Drazen, J.M. "Leukotrienes as Mediators of Airway Obstruction", *Amer. Journal of Respiratory & Critical Care Medicine*, vol. 158, 1998, pp. S193-S200.

Resnati, M. et al. "The Fibrinolytic Receptor for Urokinase Activates the G-protein-coupled Chemotactic Receptor FPRL1/LXA4R", *Proc. Nat'l. Acad. Sci.*, vol. 99, 2002, pp. 1359-1364.

Soyombo, O. et al. "Effects of Lipoxin A4 on Chemotaxis and Degranulation of Human Eosinophils Stimulated by Platelet- Activating Factor and N-formly-L-methionyl-L-leucyl-L-phenylalanine", *Allergy*, vol. 49, 1994, pp. 230-234.

Bandeira-Melo, C. et al. "Cutting Edge: Lipoxin (LX) A4 and Aspirin-Triggered 15-epi-LXA4 Block Allergen-Induced Eosinophil Trafficking", *J. Immun.*, vol. 164, 2000, pp. 2267-2271.

Bandeira-Melo, C. et al. "Cyclooxygenase-2-dervied Prostaglandin E2 and Lipoxin A4 Accelerate Resolution of Allergic Edema in Angiostrongylus Costaricensis-infected Rats: Relationship with Concurrent Eosinophilia", *J. Immun.*, vol. 164, 2000, pp. 1029-1036.

Aliberti, J. et al. "Lipoxin-Mediated Inhibition of IL-12 Production by DCs: A Mechanisn for Regulation of Microbial Immunity", *Nature Immunology*, vol. 3, 2002, pp. 76-82.

Sanak, M. et al. "Aspirin-tolerant Asthmatics Generate More Lipoxins than Aspirin-intolerant Asthmatics", *European Respiratory Journal*, vol. 16, 2000, pp. 44-49.

Godson, C. et al. "Cutting Edge: Lipoxins Rapidly Stimulate Nonphologistic Phagocytosis of Apoptotic Neutrophils by Monocyte-derived Macrophages", *J. Immun.*, vol. 164, 2000, pp. 1663-1667.

Chiang N. et al. "Leukotriene B4 Receptor Transgenic Mice Reveal Novel Protective Roles for Lipoxins and Aspirin-Triggered Lipoxins in Reperfusion", *J. Clin. Invest.*, vol. 164, 1999, pp. 309-316.

Wu, W. et al. "Eosinophils Generate Brominating Oxidants in Allergen-induced Asthma", *J. Clin. Invest.*, vol. 105, 2000, pp. 1455-1463.

Serhan, C.N. , "Lipoxin biosynthesis and its impact in inflammatory and vascular events", *Biochimica et Biophysica Acta*, 1994, pp. 1-25.

Serhan, C.N., et al., "Unorthodox routes to prostanoid formation: new twists in cyclooxygenase-initiated pathways", *J. Clin. Invest.* ,vol. 107, No. 12, 2001, pp. 1481-1489.

Elsbach, P. et al., "Role of the bactericidal/permeability-increasing protein in host defence", *Current Opinion in Immunlogy*, vol. 10, No. 1, 1998, pp. 45-49.

Ganz, T. et al., "Antimicrobial peptides of phagocytes and epithelia", *Seminars in Hematology*, vol. 34, No. 4, 1997, pp. 343-354.

Levy, O., "A neutrophil-derived anti-infective molecule: bactericidal/permeability-increasing protein", *Antimicrobial Agents and Chemotherapy*, vol. 44, No. 11, 2000, pp. 2925-2931.

Levy, O., "Antimicrobial proteins and peptides of blood: templates for novel antimicrobial agents", *Blood*,vol. 96, No. 8, 2000, pp. 2664-2672.

Beamer, L.J. et al., "Crystal structure of human BPI and two bound phospholipids at 2.4 angstrom resolution", *Science*, vol. 276, 1997, pp. 1861-1864.

Dharmsathaphorn, K. et al., "Established intestinal cell lines as model systems for electrolyte transport studies", *Methods in Enzymology*, vol. 192, 1990, pp. 354-389.

Madianos, P.N. et al., "*Porphyromonas gingivalis* infection of oral epithelium inhibits neutrophil transepithelial migration", *Infection and Immunity*, vol. 65, No. 10, 1997, pp. 3983-3990.

Lennon, P.F., et al., "Neutrophil-dervied 5'-adenosine monophosphate promotes endothelial barrier function via CD73-mediated conversaion to adenosine and endothelial $A_{2B}$ receptor activation", *J. Exp. Med.*, vol. 188, No. 8, 1998, pp. 1433-1443.

Dickson, M.A. et al., "Human keratinocytes that express hTERT and also bypass a p16$^{INK4a}$-enforced mechanism that limited life span become immortal yet retain normal growth and differentiation characteristics", *MCB* , vol. 20, No. 4, 2000, pp. 1436-1447.

Lockhart, D.J. et al., "Expression monitoring by hybridization to high-density oligonucleotide arrays", *Nature Biotechnology*, vol. 14, No. 13, 1996, pp. 1675-1680.

Taylor, C.T. et al., "Critical role of cAMP response element binding protein expression in hypoxia-elicited induction of epithelial tumor necrosis factor-a",*J. Biolog. Chem.*, vol. 274. No. 27, 1999, pp. 19447-19454.

Parkos, C.A. et al., "CD47 mediates post-adhesive events required for neutrophil migration across polarized intestinal epithelia", *J. Cell Biology*, vol. 132, 1996, pp. 437-450.

Bevilacqua, M.P. et al., "Identification of an inducible endothelial-leukocyte adhesion molecule", *Proc. Natl. Acad. Sci. USA*,vol. 84, 1987, pp. 9238-9242.

Dittel, B.N. et al., "Regulation of human B-cell precursor adhiesion to bone marrow stromal cells by cyokines that exert opposing effects on the expression of vascular cell adhesion molecule-1 (VCAM-1)", *Blood*, vol. 81, No. 9, 1993, pp. 2272-2282.

Weinrauch, Y. et al., "Extracellular accumulation of potently microbicidal bactericidal/permeability-increasing protein and p15s in an evolving sterile rabbit peritoneal inflammatory exudates", *J. Clin. Invest.*, vol. 95, 1995, pp. 1916-1924.

McCormick, B.A. et al., "*Salmonella typhimurium* attachment to human intestinal epithelial monolayers: transcellular signaling to subepithelial neurophils", *J. Cell Biology*, vol. 123, No. 4, 1993, pp. 895-907.

Colgan, S.P. et al., "Defective invitro motility of polymorphonuclear leukocytes of homozygotte and heterozygote Chediak-Higashi cats", *Vet. Immunol. Immunopathology*, 1992, pp. 205-227.

Colgan, S.P. et al, "Lipoxin A4 modulates transmigration of human neutrophils across intestinal epithelial monolayers", *J. Clin. Invest.*, vol. 92, 1993, pp. 75-82.

Weersink, A., et al., "Human granulocytes express a 550-kDa lipopolysaccharide-binding protein on the cell surface that is identical to the bactericidal/permeability-incresing protein", *J. Immunology*, vol. 150, No. 1, 1993, pp. 253-263.

Weiss, J. et al., "Purification and characterization of a potent bactericidal and membrane active protein from the granules of human polymorphonuclear leukocytes", *J. Biol. Chem.*, vol. 253, No. 8, 1978, pp. 2664-2672.

Gottardi, C.J. et al., "Cell surface biotinylation in the determination of epithelial membrane polarity", *J. Tiss. Cult. Meth.*, vol. 14, No. 4, 1992, pp. 173-180.

Pugin, J. et al., "Lipopolysaccharide activation of human endothelial and epithelial cells is mediated by lipopolysaccharide-binding protein and soluble CD14", *Proc. Nat. Acad. Sci. USA*, vol. 90, 1993, pp. 2744-2748.

Cotran, R.S. et al., "Endothelial adhesion molecules in health and disease", *Pathologie Biologie*, vol. 46, No. 3, 1998, pp. 164-170.

Ouellette, A.J., "Mucosal immunity and inflammation IV. paneth cell antimicrobial peptides and the biology of the mucosal barrier", *Am. J. Physiol.*, vol. 40, No. 2, 1999, pp. G257-G261.

Harwig, S. et al., Bacterial properties of murine intestinal phospholipase $A_2$, *J. Clin. Invest.*, vol. 95, 1995, pp. 603-610.

Imler, J.L. et al., "Toll receptors in innate immunity", *TRENDS in Cell Biology*, vol. 11, No. 7, 2001, pp. 304-311.

Cario, E. et al., "Differential alteration in intestinal epithelial cell expression of toll-like receptor # (TLR3) and TLR4 in inflammatory bowel disease", *Infection and Immunity*, vol. 68, No. 12, 2000, pp. 7010-7017.

Wong, P.K. et al., "Lipoxins inhibit microvascular inflammatory actions of leukotriene $B_4$", *Cell-Cell Interactions in the Release of Inflammatory Mediatiors*, 1991, pp. 185-192.

Pouliot, M. et al., "Lipoxin A4 analogues inhibit leukocyte recruitment to *Porphromonas gingivalis*: a role for cycloosygenase-2 and lipoxins in periodontal disease", *Biochemistry*, vol. 39, No. 16, 2000, pp. 4761-4768.

Dubois, R.N. et al., "Cyclooxygenase in biology and disease", *FASEB Journal*, vol. 12, 1998, pp. 1063-1073.

Nisengard, R.J. et al., "Peridontal disease", *Oral Microbiology and Immunology*, vol. 2, 1994, pp. 360-384.

Sartor, R.B., "Microbial factors in the pathogenesis of Crohn's disease, ulcerative colitis, and experimental intestinal inflammation", *Inflammatory Bowel Disease*, Fourth Edition, 1995, pp. 96-124.

Monajemi, H. et al., "Inflammatory bowel disease is associated with increased mucosal levels of bactericidal/permeability-increasing protein", *Gastroenterology*, vol. 110. No. 3, 1996, pp. 733-739.

Haapamaki M.M., et al., "Bactericidal/permeability-increasing protein in colonic mucosa in ulcerative colitis", *Hepato-Gastroenterology*, vol. 46, 1999, pp. 2273-2277.

Stoffel, M.P. et al., "Anti-neutrophil cytoplasmic antibodies (ANCA) directed against bactericidal/permeability increasing protein (BPI): a new seromarker for inflammatory bowel disease and associated disorders", *Clin. Exp. Immunology*, vol. 104, 1996, pp. 54-59.

Levin, M. et al., "Recominant bactericidal/permeability-increasing protein (rBPI$_{21}$) as adjunctive treatment for children with severe meningococcal spsis: a randomised trial", *Lancet*, vol. 356, No. 9234, 2000, pp. 961-967.

Levy, O. et al., "Bactericidal/permeability-increasing protein in host defense and its efficacy in the treatment of bacterial sepsis", *Curr. Infect. Dis. Reports*, vol. 3, 2001, pp. 407-412.

Levy, O. "Therapeutic potential of the bactericidal/permeability-increasing protein", *Expert Opin. Investig. Drugs*, 2002, pp. 159-167.

International Search Report for PCT/US02/40620 mailed May 13, 2003.

Elshbach et al. 1998, Current opinion in immunology, vol. 10: 45-49.

Canny et al. PNAS, Mar. 19, 2002, vol. 99(6); 3902-3907.

1333CA:3608, Pouliot et al, 2000.

Peuliot, M. et al., Lipoxin A4 analogues inhibit leukocyte recruitment to *Porphromonas gingivalis*: a role for cycloosygenase-2 and lipoxins in periodontal disease, *Biochemistry*, vol. 39, No. 16, 2000, pp. 4761-4768.

APPROACH TO ANTI-MICROBIAL HOST DEFENSE WITH MOLECULAR SHIELDS WITH LIPOXIN COMPOUNDS

CROSS-REFERENCE TO RELATED APPLICATION(S)

The application is a Continuation of U.S. patent application Ser. No. 10/323,591, filed Dec. 18, 2002, which claims benefit of U.S. Provisional Patent Application No. 60/342,138, filed Dec. 18, 2001, the contents of which are incorporated herein by reference.

STATEMENT REGARDING FEDERALLY SPONSORED RESEARCH

The work leading to this invention was supported in part by National Institutes of Health (NIH) grants RO-1 DK50189 and PO-1 DE13499. The U.S. Government therefore may have certain rights in the invention.

BACKGROUND

During both acute and chronic inflammatory processes, epithelial cells coordinate mucosal responses to infection. For this reason, much recent attention has been paid to understanding innate, anti-inflammatory pathways utilized by mucosal epithelial cells. Of particular interest are a group of lipid mediators termed the lipoxins (1). Lipoxins are bioactive molecules derived from membrane arachidonic acid by the combined action of 5-lipoxygenase (LO) and 12-LO or 15-LO (2). A number of recent in vitro and in vivo studies have revealed that lipoxins, and specifically lipoxin $A_4$ ($LXA_4$), function as innate "stop signals", serving to control local inflammatory processes (3). Synthetic lipoxin analogs exhibit greater potency for these actions than the native compound, due to decreased metabolism to inactive compounds (4).

The initial encounter of microbes with human tissues and cells occurs at the level of mucosal tissues. Epithelial cells line all mucosal organs, and thus, the epithelium is the key interface for microbial interactions. Importantly, microorganisms which interact with mucosal surfaces may be beneficial (e.g. normal flora) or pathogenic (e.g. infectious agents), and as a result, epithelial cells have adapted mechanisms to selectively kill or inactivate invading microorganisms. As part of this arsenal, epithelial cells express antimicrobial peptides whose primary function includes killing of invading microorganisms. This family of unrelated peptides includes peroxidase, lactoferrin, lysozyme, phospholipase A2, secretory leukoprotease inhibitor (SLPI), and defensins (1A). Among the innate anti-inflammatory and/or anti-infective defense molecules of humans is the bactericidal/permeability-increasing protein (BPI), a 55-60 kDa protein found in neutrophil azuorphilc granules, on the neutrophil cell surface, and to a lesser extent, in specific granules of eosinophils (7-9). BPI selectively exerts multiple anti-infective actions against gram-negative bacteria, including cytotoxicity through damage to bacterial inner/outer membranes, neutralization of bacterial lipopolysaccharide (endotoxin), as well as serving as an opsonin for phagocytosis of gram-negative bacteria by neutrophils (8, 10). Structural characterization of BPI reveals a symmetrical bipartite molecule containing a cationic N-terminal region for antibacterial and endotoxin neutralization and a C-terminal motif necessary for bacterial opsonization (11).

Therefore, a need exists for the stimulation, production, and/or release of BPI from body tissues to help combat, for example, bacterial invasion and/or infection.

SUMMARY

Epithelial cells which line mucosal surfaces are the first line of defense against bacterial invasion and infection. Recent studies have also indicated that epithelial cells contribute significantly to the orchestration of ongoing inflammatory processes. The present invention provides that antimicrobial peptides expressed by human epithelial cells, including BPI (an antibacterial and endotoxin-neutralizing molecule previously associated with neutrophils), can be stimulated and its production increased in the presence of the compounds of the invention, discussed vide infra. Moreover, epithelial cells express antimicrobial peptides whose primary function includes killing of invading microorganisms. This family of unrelated peptides includes peroxidase, lactoferrin, lysozyme, phospholipase A2, secretory leukoprotease inhibitor (SLPI), and defensins (1A). The present invention is intended to include the use of compounds presented herein for interaction with the peroxidase, lactoferrin, lysozyme, phospholipase A2, secretory leukoprotease inhibitor (SLPI), and defensins (1A) and including BPI.

Moreover, the present invention provides that epithelial antimicrobial peptides, such as BPI, are transcriptionally regulated transcriptionally regulated by analogs of endogenously occurring anti-inflammatory molecules (aspirin-triggered lipoxins, ATLa). Initial studies to verify microarray analysis revealed that epithelial cells of wide origin (oral and intestinal mucosa) express BPI and each is similarly regulated by ATLa. Studies aimed at localization of BPI revealed that such expression occurs on the cell surface of cultured epithelial cell lines and dominantly localizes to epithelia in human mucosal tissue. Functional studies employing a BPI-neutralizing anti-serum revealed that surface BPI blocks endotoxin-mediated signaling in epithelia and kills *Salmonella typhimurium*. These studies identify a previously unappreciated "molecular shield" for protection of mucosal surfaces against Gram-negative bacteria and their endotoxin.

Experiments aimed at identifying new anti-inflammatory molecules on mucosal surfaces revealed that epithelial cells express surface BPI; the expression of which was regulated by epithelial exposure to stable analogs of aspirin-triggered lipoxins. Epithelial BPI was found to promote bacterial killing and to diminish endotoxin activation of epithelia. These results identify a new pathway by which anti-inflammatory molecules enhance anti-microbial and endotoxin-neutralizing activity through transcriptional activation of BPI, heretofore solely associated with phagocytes.

It has been surprisingly discovered that lipoxins (LX's), i.e., lipoxin analogs, and aspirin-triggered lipoxins (ATLa's) of the invention, discussed infra, can be utilized for the stimulation and increased secretion of bactericidal permeability increasing protein (BPI) from various tissues, i.e., mucosal cells, epithelial cells, for combating infection and/or the invasion of bacteria in a subject. For example, synthetic analogs [e.g., 15-epi-16-(parafluoro)-phenoxy-$LXA_4$ (ATLa) (5)] modeled on 15-epi-$LXA_4$, a native lipoxin generated in vivo in the presence of aspirin via COX-2 acetylation (6), contribute in part to the anti-inflammatory actions of aspirin. Consequently, the compounds disclosed herein are useful for the treatment and prevention of infection by bacteria in a subject.

According to one aspect of the invention, increased production or release of BPI protein by a subject's tissue(s), stimulated by one or more compounds of the invention, provide alleviation of many disease states or conditions associated with endotoxin mediated effects. For example, such endotoxin mediated effects include, but are not limited to: increases in circulating tumor necrosis factor (TNF), soluble TNF receptors p55 and p75 (sTNFr (p55) and sTNFr (p75)), interleukin 6 (IL-6), interleukin 8 (IL-8), interleukin 10 (IL-10) and increased neutrophil degranulation characterized by increased circulating lactoferrin and/or elastase/alpha 1 antitrypsin complexes (EAA); increases in circulating tissue plasminogen activator antigen (tPA Ag), tissue plasminogen activator activity (tPA act), and alpha 2-plasmin inhibitor-plasmin (PAP) complexes, plasminogen activator inhibitor antigen (PAI Ag) and urokinase type plasminogen activator (uPA); decrease in lymphocytes; increases in thrombin/antithrombin III (TAT) complexes; and decreases in systemic vascular resistance index (SVRI) and increases in cardiac index (CI).

BPI is a potent and specific bactericidal compound. The disease targets include, for example, sepsis and infectious diseases, and provide a non-antibiotic mechanism to fight infectious disease caused by Gram negative bacteria. Therefore, use of the therapeutic compounds of the invention to stimulate production of BPI by a subject, helps to treat, ameliorate, or prevent such disease.

According to another aspect of the invention, increased production or release of BPI protein by a subject's tissue(s), stimulated by one or more of the BPI inducing agents of the invention, provides for the use of a BPI protein inducing agent in the manufacture of a medicament for treatment of humans exposed to bacterial endotoxin. This aspect of the invention contemplates use of at least one BPI protein inducing agent in the manufacture of such medicaments in an therapeutically effective amount to alleviate endotoxin in tumor necrosis factor and interleukin 6; in an amount effective to alleviate endotoxin mediated increase in circulating interleukin 8 and in neutrophil degranulation as characterized by increased circulating lactoferrin and/or elastase/alpha 1 antitrypsin complexes; in an amount effective to alleviate endotoxin mediated changes in numbers of circulating lymphocytes; in an amount effective to alleviate endotoxin mediated increase in circulating tissue plasminogen activator and tissue plasminogen activator activity; in an amount effective to alleviate endotoxin-mediated decreases in systemic vascular resistance index; in an amount effective to treat sepsis; and in an amount effective to bacterial infections. This aspect of the invention further contemplates use of a BPI protein inducing agents in combination with bacterial antibiotics in the manufacture of such medicaments.

In another aspect, the present invention is directed to a packaged pharmaceutical composition for treating the activity or conditions described herein in a subject. The packaged pharmaceutical composition includes a container holding a therapeutically effective amount of at least one therapeutic compound of the invention, i.e., a BPI inducing agent, having one of the formulae described infra and instructions for using the therapeutic compound for treating the activity or condition in the subject.

BRIEF DESCRIPTION OF THE DRAWINGS

The invention will be more fully understood from the following detailed description taken in conjunction with the accompanying drawings, in which.

DETAILED DESCRIPTION

Figure 1:
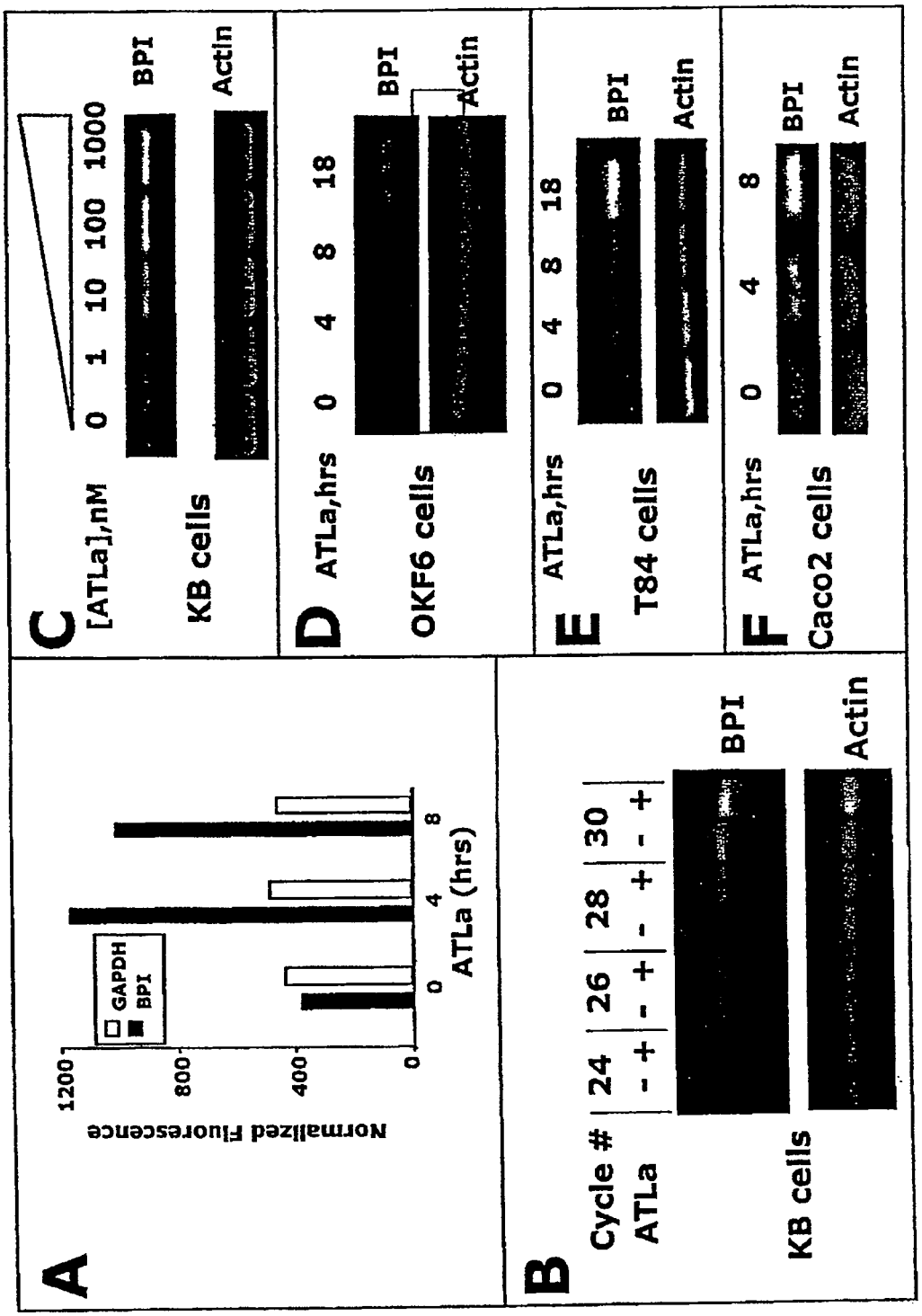
FIG. 1 depicts BPI induction by ATLa. Confluent epithelial monolayers were exposed to indicated concentrations or time periods of ATLa (1 µM). Panel A demonstrates quantitative microarray data for BPI in epithelial cells exposed to indicated conditions. In panel B, total RNA was isolated from ATLa-exposed KB cells (1 µM, 8 h), and examined for BPI transcript by semi-quantitative RT-PCR (increasing numbers of PCR cycles). β actin transcript was examined under similar conditions as an internal standard. In panel C, KB cells were exposed to indicated concentrations of ATLa for 8 hr and examined for BPI transcript using 28 cycles of PCR. In panels D-F, indicated epithelial cell lines were exposed to indicated periods of ATLa and BPI transcript was determined by 26 cycles of RT-PCR. β actin transcript was used as an internal standard.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Abbreviations used throughout the present application include the following and are included here for convenience. ATL, aspirin-triggered 15-epi-LX, 15 R-LX; COX, cyclooxygenase I, II (isoforms); EC, endothelial cells; LC/S/MS, liquid chromatography tandem mass spectrometry; LO, lipoxygenase; LT, leukotriene; LX, lipoxin; PG, prostaglandins; PMN, polymorphonuclear leukocyte; HETE, hydroxyeicosatetraenoic acid; $LXA_4$, 5S,6R,15S-trihydroxy-7,9,13-trans-11-cis-eicosatetraenoic acid; 15-epi-$LXA_4$, 5S,6R,15R-trihydroxy-7,9,13-trans-11-cis-eicosatetraenoic acid; and C20:4 (arachidonic acid, AA, an ω-6 fatty acid).

It has been surprisingly discovered that lipoxins (LX's) and aspirin-triggered lipoxins (ATLa's) of the invention, discussed infra, can be utilized for the stimulation, release and increased secretion of bactericidal permeability increasing protein (BPI) from various tissues, i.e., mucosal cells, epithelial cells, for combating infection and/or the invasion of bacteria in a subject. Consequently, the compounds disclosed herein are useful for the treatment and prevention of infection in a subject.

According to one aspect of the invention, increased production or release of BPI protein by a subject's tissue(s), stimulated by one or more compounds of the invention, provide alleviation of many disease states or conditions associated with endotoxin mediated effects. For example, such endotoxin mediated effects include, but are not limited to: increases in circulating tumor necrosis factor (TNF), soluble TNF receptors p55 and p75 (sTNFr (p55) and sTNFr (p75)), interleukin 6 (IL-6), interleukin 8 (IL-8), interleukin 10 (IL-10) and increased neutrophil degranulation characterized by increased circulating lactoferrin and/or elastase/alpha 1 antitrypsin complexes (EAA); increases in circulating tissue plasminogen activator antigen (tPA Ag), tissue plasminogen activator activity (tPA act), and alpha 2-plasmin inhibitor-plasmin (PAP) complexes, plasminogen activator inhibitor antigen (PAI Ag) and urokinase type plasminogen activator (uPA); decrease in lymphocytes; increases in thrombin/anti-thrombin III (TAT) complexes; and decreases in systemic vascular resistance index (SVRI) and increases in cardiac index (CI).

BPI is a potent and specific bactericidal compound. The disease targets include, for example, sepsis and infectious diseases. The present invention provide a non-antibiotic mechanism to fight infectious disease caused by Gram negative bacteria. Therefore, use of the therapeutic compounds of the invention to stimulate production of BPI by a subject, helps to treat, ameliorate, or prevent such disease.

According to another aspect of the invention, increased production or release of BPI protein by a subject's tissue(s), stimulated by one or more of the compounds of the invention, provides for the use of a BPI protein inducing agent, i.e., the compounds of the invention, for the manufacture of a medicament for treatment of humans exposed to bacterial endotoxin. This aspect of the invention contemplates use of at least one BPI protein inducing agent in the manufacture of such medicaments in an amount effective to alleviate endotoxin in tumor necrosis factor and interleukin 6; in an amount effective to alleviate endotoxin mediated increase in circulating interleukin 8 and in neutrophil degranulation as characterized by increased circulating lactoferrin and/or elastase/alpha 1 antitrypsin complexes; in an amount effective to alleviate endotoxin mediated changes in numbers of circulating lymphocytes; in an amount effective to alleviate endotoxin mediated increase in circulating tissue plasminogen activator and tissue plasminogen activator activity; and in an amount effective to alleviate endotoxin-mediated decreases in systemic vascular resistance index. This aspect of the invention further contemplates use of a BPI protein inducing agents in combination with bacterial antibiotics in the manufacture of such medicaments.

The phrase "BPI inducing agent" is intended to include those compounds which cause BPI to be released from tissue(s), which cause the production of BPI to be increased relative to the normal stasis of the subject's physiology or stimulates production of BPI, or combinations thereof. In general, these compounds include lipoxins and lipoxin analogs and aspirin triggered lipoxins and analogs. These inducing agents cause BPI to become more readily available within the subject to combat disease or infection which results from the disease process. Therefore, the compounds of the invention indirectly act upon the disease process by stimulating the increased production and/or release of BPI which in turn prophylactically or therapeutically treats the disease. As described above, the disease process may be associated with bacteria. Therefore, the compounds are useful for the treatment of these conditions such that the physiological effects associated with the disease state or condition are inhibited, decreased, or eradicated.

Lipoxins

In one aspect, lipoxins and lipoxin analogs useful as BPI inducing agents in treatment of the maladies described throughout this specification have the formulae encompassed by U.S. Pat. Nos. 4,560,514, 5,441,951, 5,648,512, 5,650,435, and 6,048,897, the contents of which are incorporated herein by reference in their entirety. For example, lipoxin analogs encompassed by the present invention include those having the following characteristics.

The instant lipoxins comprising an "active region" and a "metabolic transformation region" as both terms are defined herein are generally of the following structure:

wherein $R_1$ can be

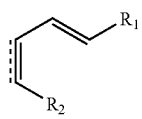

wherein $R_1$ can be

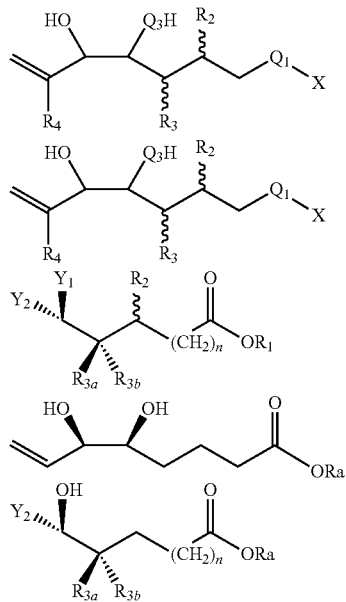

and $R_2$ can be

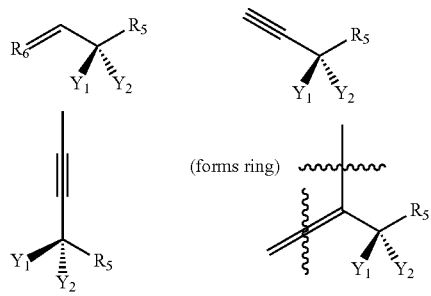

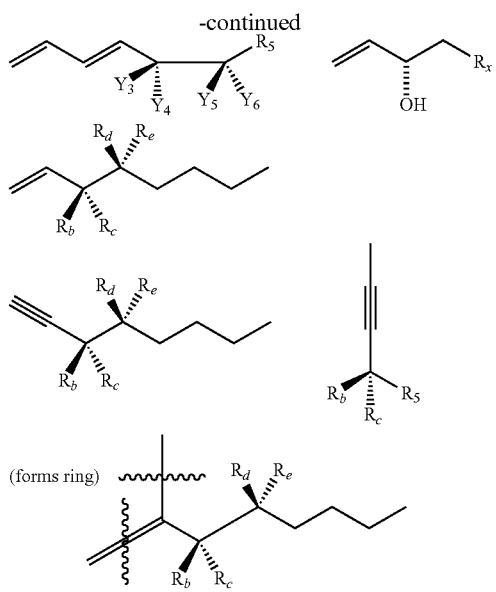

In one embodiment, the lipoxin analogs of this invention have the following structural formula I:

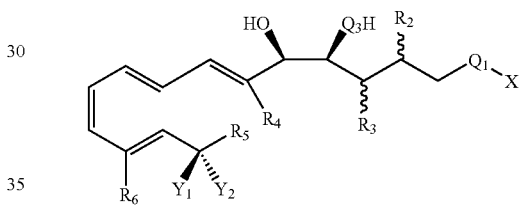

wherein X is $R_1$, $OR_1$, or $SR_1$;

wherein $R_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl

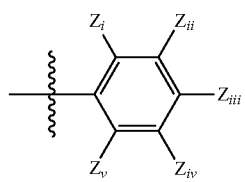

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN);
wherein $Q_3$ is O, S or NH;
wherein one of $R_2$ and $R_3$ is a hydrogen atom and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;
wherein $R_4$ is
(a) a hydrogen atom;
(b) an alkyl of 1 to 6 carbon atoms, inclusive, which can be straight chain or branched;
wherein $Y_1$ or $Y_2$ is —OH, methyl, or —SH and wherein the other is
(a) a hydrogen atom
(b) $CH_aZ_b$
where a+b=3, a=0 to 3, b=0 to 3; and
each Z, independently, is a cyano, a nitro, or a halogen atom;
(c) an alkyl of 2 to 4 carbon atoms, inclusive, straight chain or branched; or
(d) an alkoxy of 1 to 4 carbon atoms, inclusive;
or $Y_1$ and $Y_2$ taken together are
(a) =NH; or
(b) =O;
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) a cycloalkyl of 3 to 10 carbon atoms, inclusive;
(ii) a phenyl; or
(iii) substituted phenyl

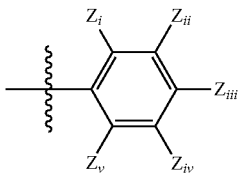

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) $R_aQ_aR_b$
wherein $Q_a$ is O or S;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
(d) —C($R_{iii}$)($R_{iv}$)—$R_i$
wherein $R_{iii}$ and $R_{iv}$ are each, independently:
(i) a hydrogen atom;
(ii) $CH_aZ_b$ where a+b=3, a=0 to 3, b=0+3, and wherein each Z, independently, is a cyano, a nitro, or a halogen atom;
(e) a haloalkyl of 1 to 8 carbon atoms, inclusive, and 1 to 6 halogen atoms, inclusive, straight chain or branched; and
wherein $R_6$ is
(a) a hydrogen atom;
(b) an alkyl from 1 to 4 carbon atoms, inclusive, straight chain or branched;
(c) a halogen.
In one embodiment of this invention, the lipoxin analogs have the following structure II:

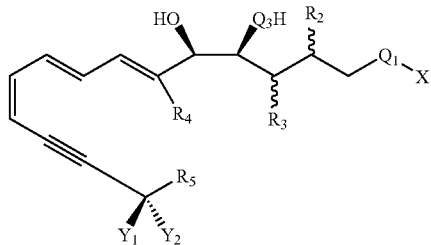

wherein X is $R_1$, $OR_1$, or $SR_1$; wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) a phenyl;
(vi) substituted phenyl

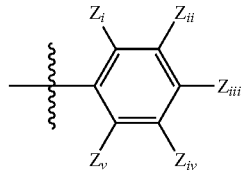

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule, such as but not limited to fluorescent labels; or
(viii) an alkenyl of 2 to 8 carbon atoms, inclusive, straight chain or branched;
wherein $Q_1$ is (C=O), $SO_2$ or (C=N);
wherein $Q_3$ is O, S or NH;
wherein one of $R_2$ and $R_3$ is hydrogen and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;

wherein $R_4$ is (a) a hydrogen atom;

(b) alkyl of 1 to 6 carbon atoms, inclusive, which can be straight chain or branched;

wherein $Y_1$ or $Y_2$ is —OH, methyl, —H or —SH and wherein the other is (a) a hydrogen atom;

(b) $CH_aZ_b$ where $a+b=3$, $a=0$ to 3, $b=0$ to 3 wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive; or $Y_1$ and $Y_2$ taken together are (a) =NH; or (b) =O;

wherein $R_5$ is (a) an alkyl of 1 to 9 carbon atoms which can be straight chain or branched;

(b) —$(CH_2)_n$—$R_i$ wherein $n=0$ to 4 and $R_i$ is (i) a cycloalkyl of 3 to 10 carbon atoms, inclusive;

(ii) phenyl; or (iii) substituted phenyl

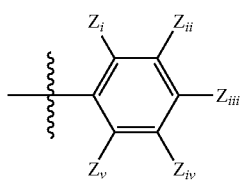

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) —$R_aQ_aR_b$ wherein $Q_a$ is —O— or —S—; and wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched;

(d) —$C(R_{iii})(R_{iv})$—$R_i$ wherein $R_{iii}$ and $R_{iv}$ are each independently:

(i) a hydrogen atom; or (ii) $CH_aZ_b$ where $a+b=3$, $a=0$ to 3, $b=0+3$ wherein each Z, independently, is a cyano, a nitro, or a halogen atom, (e) a haloalkyl of 1 to 8 carbon atoms, inclusive, and 1 to 6 halogen atoms, inclusive, straight chain or branched.

In one embodiment of this invention, the lipoxin analogs have the following structure III:

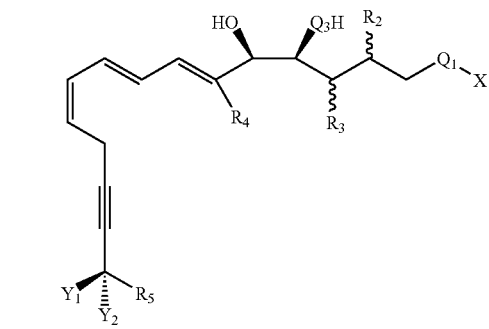

wherein X is $R_1$, $OR_1$, or $SR_1$; wherein $R_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl

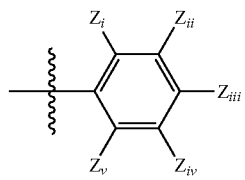

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(vii) a detectable label molecule; or (viii) an alkenyl of 2 to 8 carbon atoms, inclusive, straight chain or branched;

wherein $Q_1$ is (C=O), $SO_2$ or (C=N);

wherein $Q_3$ is O, S or NH;

wherein one of $R_2$ and $R_3$ is hydrogen atom and the other is (a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched;

wherein $R_4$ is (a) a hydrogen atom; or (b) an alkyl of 1 to 6 carbon atoms, inclusive, which can be straight chain or branched;

wherein $Y_1$ or $Y_2$ is hydroxyl, methyl, hydrogen or thiol and wherein the other is (a) a hydrogen atom;

(b) $CH_aZ_b$ where $a+b=3$, $a$ 0 to 3, $b=0$ to 3 wherein each Z, independently, is a cyano, a nitro, or a halogen atom;

(c) an alkyl of 2 to 4 carbon atoms, inclusive, straight chain or branched;
(d) an alkoxy of 1 to 4 carbon atoms, inclusive; or $Y_1$ and $Y_2$ taken together are
(a) =NH; or
(b) =O; and
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) cycloalkyl of 3 to 10 carbon atoms, inclusive;
(ii) phenyl;
(iii) substituted phenyl

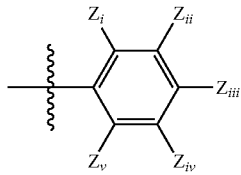

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) $R_aQ_aR_b$
wherein $Q_a$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched; or
(d) —C($R_{iii}$)($R_{iv}$)—$R_i$
wherein $R_{iii}$ and $R_{iv}$ are each independently:
(i) a hydrogen atom; or
(ii) $CH_aZ_b$ where a+b=3, a=0 to 3, b=0+3
wherein each Z, independently, is a cyano, a nitro, or a halogen atom,
(e) a haloalkyl of 1 to 8 carbon atoms, inclusive, and 1 to 6 halogen atoms, inclusive, straight chain or branched.

In another embodiment of this invention, lipoxin analogs have the following structural formula IV:

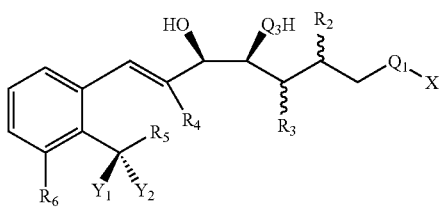

wherein X is $R_1$, $OR_1$, or $SR_1$; wherein $R_1$ is
(i) a hydrogen atom;
(ii) an alkyl of 1 to 8 carbons atoms, inclusive, which can be straight chain or branched;
(iii) a cycloalkyl of 3 to 10 carbon atoms, inclusive;
(iv) an aralkyl of 7 to 12 carbon atoms;
(v) phenyl;
(vi) substituted phenyl

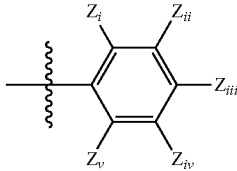

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(vii) a detectable label molecule; or
(viii) an alkenyl of 2 to 8 carbon atoms, inclusive, straight chain or branched;
wherein $Q_1$ is (C=O), $SO_2$ or (CN);
wherein $Q_3$ is O, S or NH;
wherein one of $R_2$ and $R_3$ is hydrogen and the other is
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_aQ_2R_b$
wherein $Q_2$ is —O— or —S—;
wherein $R_a$ is alkylene of 0 to 6 carbons atoms, inclusive, which can be straight chain or branched;
wherein $R_b$ is alkyl of 0 to 8 carbon atoms, inclusive, which can be straight chain or branched;
wherein $R_4$ is
(a) a hydrogen atom; or
(b) an alkyl of 1 to 6 carbon atoms, inclusive, which can be straight chain or branched;
wherein $Y_1$ or $Y_2$ is —OH, methyl, or —SH and wherein the other is
(a) a hydrogen atom;
(b) $CH_aZ_b$ where a+b=3, a=0 to 3, b=0 to 3, wherein each Z, independently, is a cyano, a nitro, or a halogen atom;
(c) an alkyl of 2 to 4 carbon atoms, inclusive, straight chain or branched; or
(d) an alkoxy of 1 to 4 carbon atoms, inclusive;
or $Y_1$ and $Y_2$ taken together are
(a) =NH; or
(b) =O;
wherein $R_5$ is
(a) an alkyl of 1 to 9 carbon atoms which can be straight chain or branched;
(b) —$(CH_2)_n$—$R_i$
wherein n=0 to 4 and $R_i$ is
(i) a cycloalkyl of 3 to 10 carbon atoms, inclusive;
(ii) phenyl; or
(iii) substituted phenyl

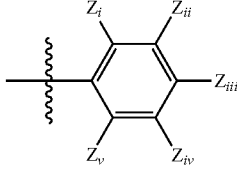

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —OR$_x$, wherein R$_x$ is 1 to 8 carbon atoms, inclusive, which can be a straight chain or branched, and hydroxyl;

(c) R$_a$Q$_a$R$_b$ wherein Q$_a$ is —O— or —S—;

wherein R$_a$ is alkylene of 0 to 6 carbons atoms, inclusive, which can be straight chain or branched;

wherein R$_b$ is alkyl of 0 to 8 carbon atoms, inclusive, which can be straight chain or branched;

(d) —C(R$_{iii}$)(R$_{iv}$)—R$_i$ wherein R$_{iii}$ and R$_{iv}$ are each independently:

(i) a hydrogen atom; or (ii) CH$_a$Z$_b$ where a+b=3, a=0 to 3, b=0+3 and wherein each Z, independently, is a cyano, a nitro, or a halogen atom; or (e) haloalkyl of 1 to 8 carbon atoms, inclusive, and 1 to 6 halogen atoms, inclusive, straight chain or branched; and wherein R$_6$ is (a) a hydrogen atom;

(b) an alkyl from 1 to 4 carbon atoms, inclusive, straight chain or branched; or (c) a halogen atom.

In another embodiment of this invention, lipoxin analogs have the following structural formula V:

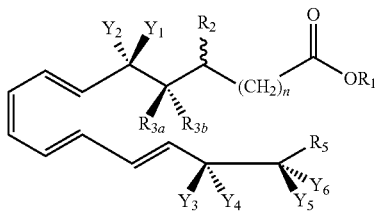

wherein R$_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl

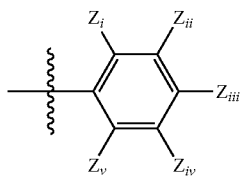

wherein Z$_i$, Z$_{ii}$, Z$_{iii}$, Z$_{iv}$ and Z$_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which can be a straight chain or branched, and hydroxyl;

(vii) a detectable label molecule; or (viii) an alkenyl of 2 to 8 carbon atoms, inclusive, straight chain or branched;

wherein n=1 to 10, inclusive;

wherein R$_2$, R$_{3a}$, and R$_{3b}$ are each independently:

(a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) R$_a$Q$_2$R$_b$ wherein Q$_2$ is —O— or —S—;

wherein R$_a$ is alkylene of 0 to 6 carbons atoms, inclusive, which can be straight chain or branched; and wherein R$_b$ is alkyl of 0 to 8 carbon atoms, inclusive, which can be straight chain or branched;

wherein Y$_1$ or Y$_2$ is —OH, methyl, hydrogen, or —SH and wherein the other is (a) a hydrogen atom;

(b) CH$_a$Z$_b$ where a+b=3, a=0 to 3, b=0 to 3, and wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or Y$_1$ and Y$_2$ taken together are (a) =NH; or (b) =O;

wherein Y$_3$ or Y$_4$ is —OH, methyl, hydrogen, or —SH and wherein the other is (a) a hydrogen atom;

(b) CH$_a$Z$_b$ wherein a+b=3, a=0 to 3, b=0 to 3, and wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or Y$_3$ and Y$_4$ taken together are (a) =NH; or (b) =O;

wherein Y$_5$ or Y$_6$ is —OH, methyl, hydrogen, or —SH and wherein the other is (a) a hydrogen atom;

(b) CH$_a$Z$_b$ where a+b=3, a=0 to 3, b=0 to 3 wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or Y$_5$ and Y$_6$ taken together are (a) =NH; or (b) =O;

wherein R$_5$ is (a) an alkyl of 1 to 9 carbon atoms which can be straight chain or branched;

(b) —(CH$_2$)$_n$—R$_i$ wherein n=0 to 4 and R$_i$ is (i) a cycloalkyl of 3 to 10 carbon atoms, inclusive;

(ii) phenyl; or (iii) substituted phenyl

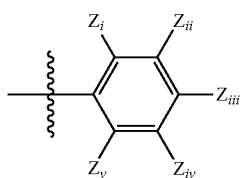

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) —$R_aQ_aR_b$ wherein $Q_a$ is —O— or —S—; and wherein $R_a$ is alkylene of 0 to 6 carbons atoms, inclusive, which can be straight chain or branched;

wherein $R_b$ is either alkyl of 0 to 8 carbon atoms, inclusive, which can be straight chain or branched or substituted phenyl;

(d) —C($R_{iii}$)($R_{iv}$)—$R_i$ wherein $R_{iii}$ and $R_{iv}$ are each independently:

(i) a hydrogen atom; or (ii) $CH_aZ_b$ where a+b=3, a=0 to 3, b=0+3, and wherein each Z, independently, is a cyano, a nitro, or a halogen atom; or (e) haloalkyl of 1 to 8 carbon atoms, inclusive, and 1 to 6 halogen atoms, inclusive, straight chain or branched.

In another embodiment of this invention, lipoxin analogs have the structural formula VI:

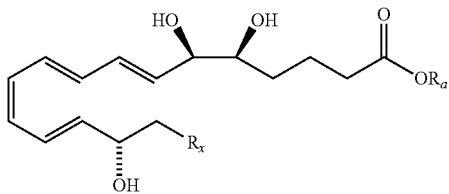

wherein $R_a$ is (a) a hydrogen atom; or (b) alkyl of 1 to 8 carbon atoms;

wherein $R_x$ is (a) substituted phenyl

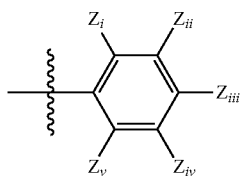

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(b) a substituted phenoxy

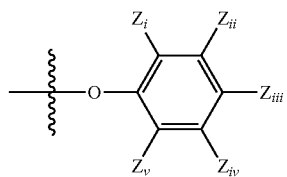

wherein $Z_i$ through $Z_v$ are as defined above; or

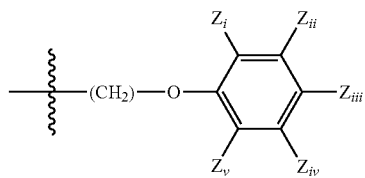

wherein $Z_i$ through $Z_v$ are as defined above.

In another preferred embodiment of this invention, lipoxin analogs have the following structural formula VII:

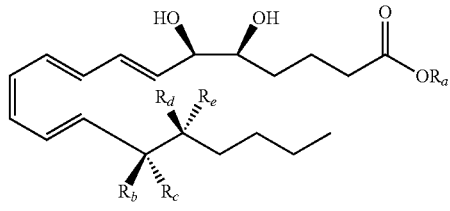

wherein $R_a$ is
(a) a hydrogen atom; or
(b) an alkyl of 1 to 8 carbon atoms;
wherein $R_b$ and $R_c$ are each independently:
(a) a hydrogen atom;
(b) a hydroxyl, or a thiol;
(c) a methyl or a halomethyl;
(d) a halogen;
(e) an alkoxy of 1 to 3 carbon atoms;
wherein $R_d$ and $R_e$ are each independently:
(a) a hydrogen atom;
(b) a hydroxyl, or thiol;
(c) a methyl or halomethyl;
(d) a halogen;
(e) an alkoxy of 1 to 3 carbon atoms; or
(f) an alkyls or haloalkyl of 2 to 4 carbon atoms, inclusive, which can be straight chain or branched.

In another preferred embodiment of this invention, the lipoxin analogs have the structural formula VIII:

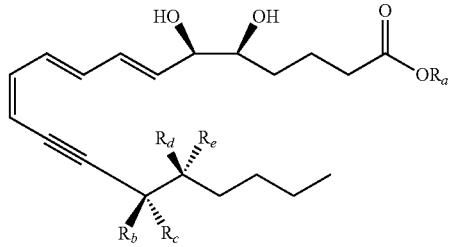

wherein $R_a$ is
 (a) a hydrogen atom; or
 (b) an alkyl of 1 to 8 carbon atoms;
wherein $R_b$ and $R_c$ are each independently:
 (a) a hydrogen atom;
 (b) a hydroxyl or a thiol;
 (c) a halomethyl;
 (d) a halogen;
 (e) an alkyl of 1 to 3 carbon atoms, inclusive, straight chain or branched; or
 (f) an alkoxy of 1 to 3 carbon atoms, inclusive;
wherein $R_d$ and $R_e$ are each independently:
 (a) a hydrogen atom;
 (b) a hydroxyl, or a thiol;
 (c) a methyl or a halomethyl;
 (d) a halogen;
 (e) an alkoxy of 1 to 3 carbon atoms, inclusive; or
 (f) an alkyl or haloalkyl of 2 to 4 carbon atoms, inclusive, which can be straight chain or branched.

In another embodiment of this invention, the lipoxin analogs have the structural formula IX:

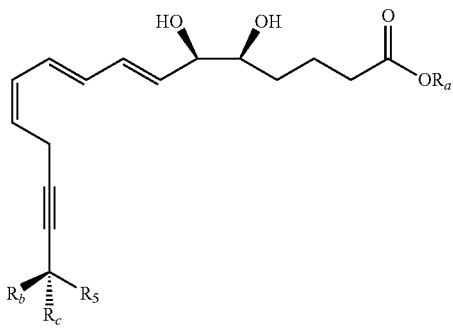

wherein $R_a$ is
 (a) a hydrogen atom; or
 (b) an alkyl of 1 to 8 carbon atoms;
wherein $R_b$ and $R_c$ are each independently:
 (a) a hydrogen atom;
 (b) a hydroxyl or thiol;
 (c) a halomethyl;
 (d) a halogen;
 (e) an alkyl of 1 to 3 carbon atoms, inclusive, straight chain or branched;
 (f) an alkoxy of 1 to 3 carbon atoms, inclusive; and
wherein $R_5$ is
 (a) an alkyl of 1 to 9 carbon atoms which can be straight chain or branched;
 (b) $-(CH_2)_n-R_i$
wherein n=0 to 4 and $R_i$ is
 (i) a cycloalkyl of 3 to 10 carbon atoms, inclusive;
 (ii) phenyl; or
 (iii) substituted phenyl

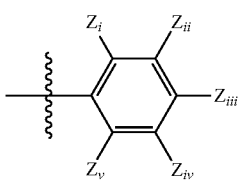

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which can be a straight chain or branched, and hydroxyl;
 (c) $R_aQ_aR_b$
wherein $Q_a$ is $-O-$ or $-S-$;
wherein $R_a$ is alkylene of 0 to 6 carbons atoms, inclusive, which can be straight chain or branched;
wherein $R_b$ is either alkyl of 0 to 8 carbon atoms, inclusive, which can be straight chain or branched or substituted phenyl;
 (d) $-C(R_{iii})(R_{iv})-R_i$
wherein $R_{iii}$ and $R_{iv}$ are each, independently:
 (i) a hydrogen atom; or
 (ii) $CH_aZ_b$ where a+b=3, a=0 to 3, b=0+3
wherein each Z, independently, is a cyano, a nitro, or a halogen atom; or
 (e) haloalkyl of 1 to 8 carbon atoms, inclusive, and 1 to 6 halogen atoms, inclusive, straight chain or branched.

In another preferred embodiment, the compounds have the structural formula X:

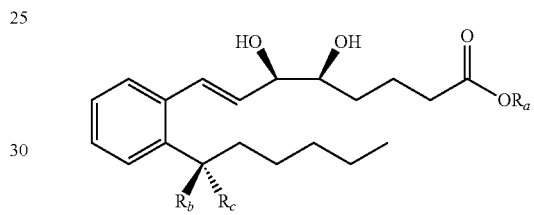

wherein $R_a$ is
 (a) a hydrogen atom; or
 (b) alkyl of 1 to 8 carbon atoms, inclusive, straight chain or branched; and
wherein $R_b$ and $R_c$ are each, independently:
 (a) a hydrogen atom;
 (b) a hydroxyl or a thiol;
 (c) a halomethyl;
 (d) a halogen;
 (e) an alkyl of 1 to 3 carbon atoms, inclusive, straight chain or branched;
 (f) an alkoxy of 1 to 3 carbon atoms, inclusive.

In another preferred embodiment, the compounds have the structural formula XI:

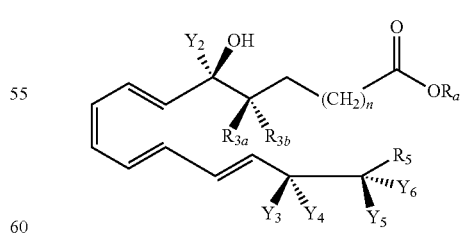

wherein $R_a$ is
 (i) a hydrogen atom;
 (ii) an alkyl of 1 to 8 carbons atoms, inclusive, which can be straight chain or branched; or
 (iii) a detectable label molecule;

wherein n=1 to 10, inclusive;
wherein $Y_2$, $R_{3a}$, and $R_{3b}$ are each, independently:
(a) a hydrogen atom;
(b) an alkyl of 1 to 8 carbon atoms, inclusive, which can be straight chain or branched;
(c) a cycloalkyl of 3 to 6 carbon atoms, inclusive;
(d) an alkenyl of 2 to 8 carbon atoms, inclusive, which can be straight chain or branched; or
(e) $R_a Q_2 R_b$
wherein $Q_2$ is —O— or —S—;
wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;
wherein $Y_1$ is —OH, methyl, or —SH;
wherein $Y_2$ is
(a) a hydrogen atom;
(b) $CH_a Z_b$
where a+b=3, a=0 to 3, b=0 to 3
wherein each Z, independently, is a cyano, a nitro, or a halogen atom; or
(c) an alkyl of 2 to 4 carbon atoms, inclusive, straight chain or branched;
wherein $Y_3$ and $Y_5$ are each independently:
(a) a hydrogen atom;
(b) $CH_a Z_b$
wherein a+b=3, a=0 to 3, b=0 to 3 and wherein each Z, independently, is a cyano, a nitro, or a halogen atom; or
(c) an alkyl of 2 to 4 carbon atoms, inclusive, straight chain or branched;
wherein $Y_4$ and $Y_6$ are each, independently
(a) a hydrogen atom;
(b) an alkyl of 2 to 4 carbon atoms, inclusive, straight chain or branched;
(c) an alkoxy of 1 to 4 carbon atoms, inclusive, straight chain or branched; or
(d) a hydroxyl or thiol; and
wherein $R_5$ is
(a) an alkyl of 1 to 9 carbon atoms which can be straight chain or branched;
(b) —$(CH_2)_n R_i$
wherein n=0 to 3 and $R_i$ is
(i) a cycloalkyl of 3 to 10 carbon atoms, inclusive;
(ii) phenyl;
(iii) substituted phenyl

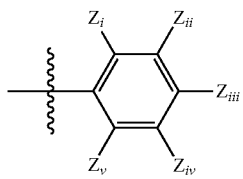

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(c) —$R_a Q_a R_b$
wherein $Q_a$ is —O— or —S—;
wherein $R_a$ is alkylene of 0 to 6 carbons atoms, inclusive, which can be straight chain or branched;
wherein $R_b$ is
(a) a substituted phenyl

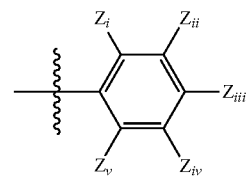

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(b) a substituted phenoxy

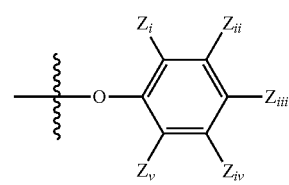

wherein $Z_i$ through $Z_v$ are as defined above; or

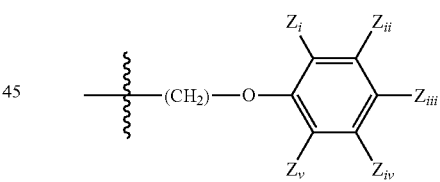

wherein $Z_i$ through $Z_v$ are as defined above;
(d) a haloalkyl of 1 to 8 carbon atoms, inclusive, and 1 to 6 halogen atoms, inclusive, straight chain or branched.

In certain embodiments of this invention, the compounds of this invention have the following structural formulas:

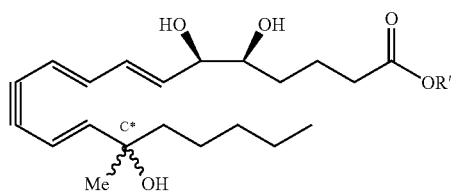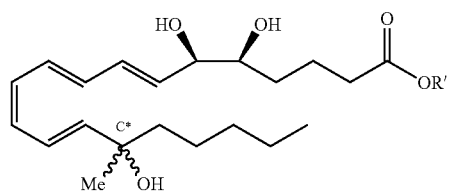

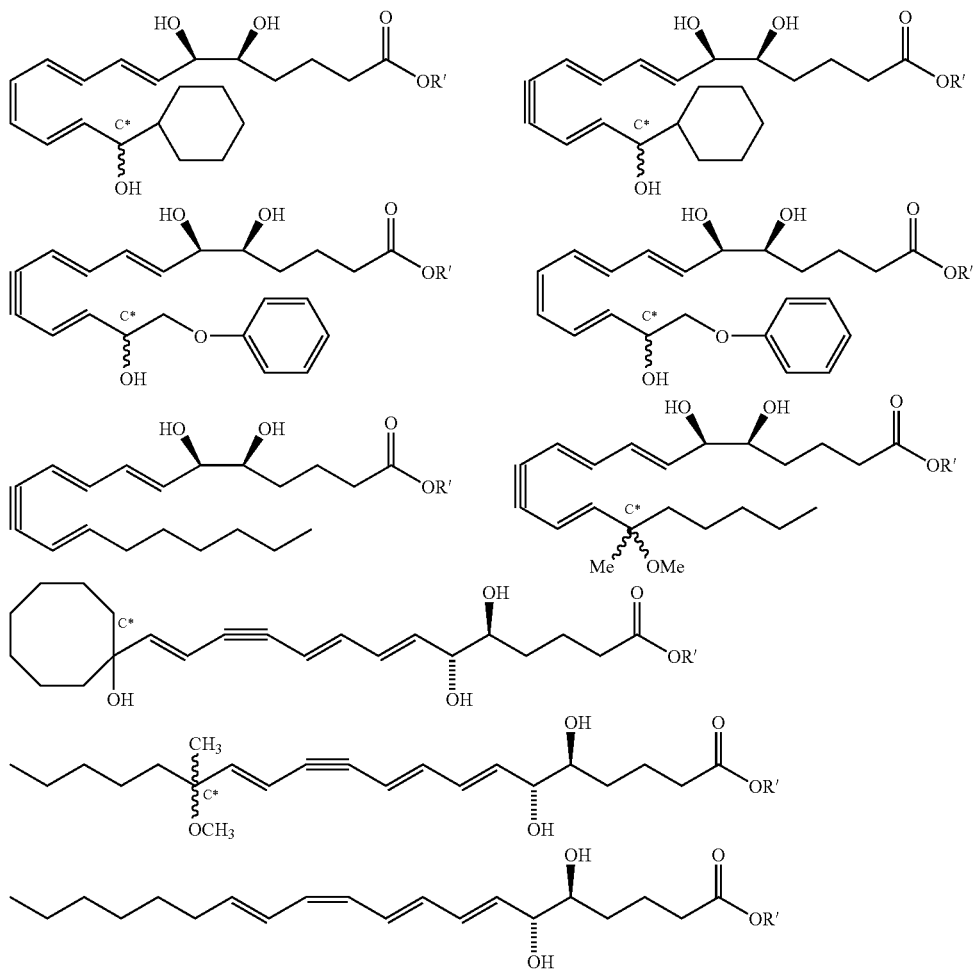
where R' is H or CH$_3$; and where the substituents at C* are in the R configuration.
In other preferred embodiments of this invention, the compounds of this invention have the following structural formulas:
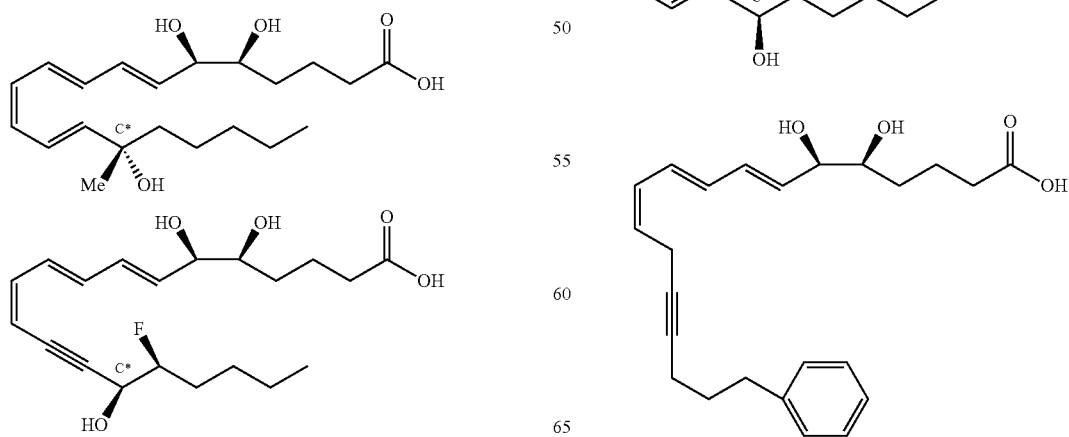
-continued -continued

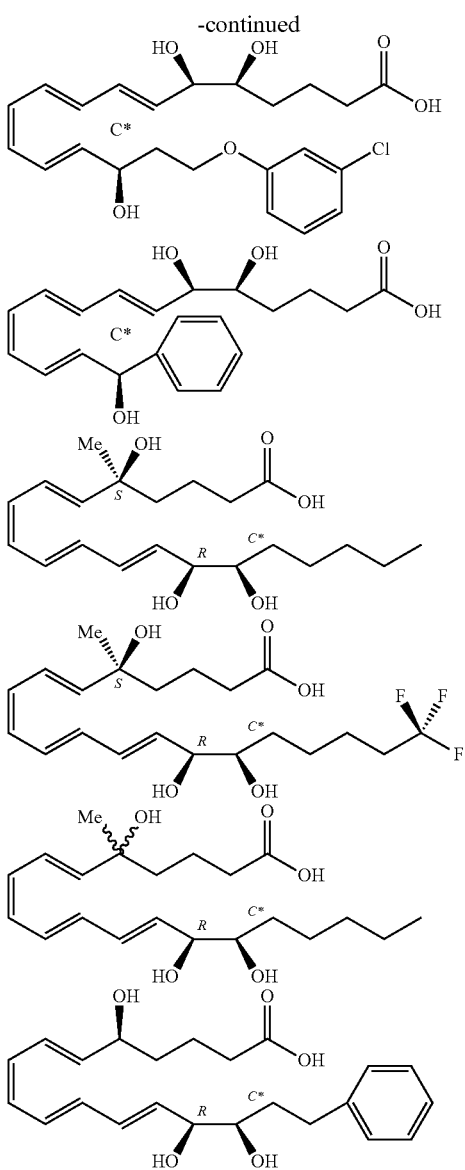

where the substitutents at the C* are in the R configuration.

It is to be understood that the carboxylic acids and esters of the invention can be converted, if necessary, into pharmaceutically acceptable salts.

Lipoxins Having Phenoxy or Thiophenoxy Substituents

In another aspect, lipoxins and lipoxin analogs useful as a BPI inducing agent in the treatment of the maladies, disease states or conditions described throughout the specification has the formula:

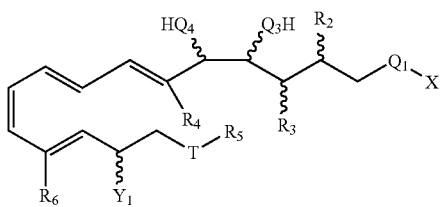

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

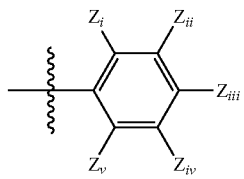

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

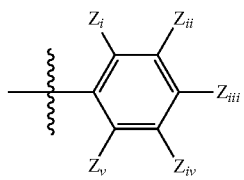

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof.

In yet another aspect, lipoxins and lipoxin analogs useful as a BPI inducing agent in the treatment of the maladies, disease states or conditions described throughout the specification has the formula:

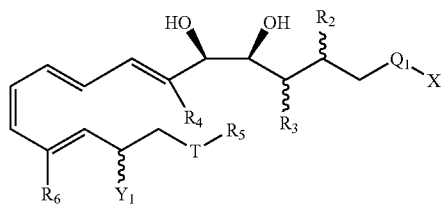

wherein X is $R_1$, $OR_1$, or $SR_1$;

wherein $R_1$ is (i) a hydrogen atom;

(ii) an alkyl of 1 to 8 carbon atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

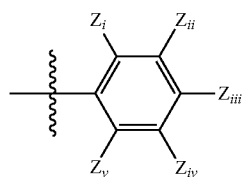

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is (a) H;

(b) an alkyl of 1 to 8 carbon atoms, inclusive, which may be a straight chain or branched;

(c) a cycloalkyl of 3 to 6 carbon atoms, inclusive;

(d) an alkenyl of 2 to 8 carbon atoms, inclusive, which may be straight chain or branched; or (e) $R_aQ_2R_b$ wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is (a) H;

(b) an alkyl of 1 to 6 carbon atoms, inclusive, which may be a straight chain or branched;

wherein $R_5$ is

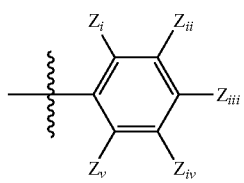

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is $-OH$, methyl, $-SH$, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is (a) H;

(b) an alkyl from 1 to 4 carbon atoms, inclusive, straight chain or branched;

wherein T is O or S, and pharmaceutically acceptable salts thereof.

In still another aspect, lipoxins and lipoxin analogs useful as a BPI inducing agent in the treatment of the maladies, disease states or conditions described throughout the specification has the formula:

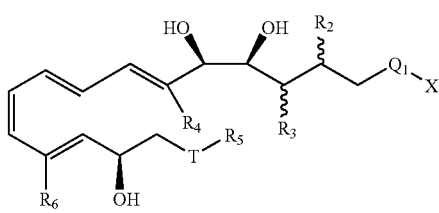

wherein X is $R_1$, $OR_1$, or $SR_1$;

wherein $R_1$ is (i) a hydrogen atom;

(ii) an alkyl of 1 to 8 carbon atoms, inclusive, which may be straight chain or branched;

(iii) a cycloalkyl of 3 to 10 carbon atoms;

(iv) an aralkyl of 7 to 12 carbon atoms;

(v) phenyl;

(vi) substituted phenyl

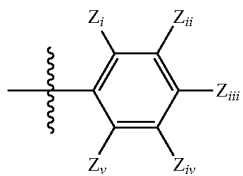

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
   (vii) a detectable label molecule; or
   (viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
   (a) H;
   (b) an alkyl of 1 to 8 carbon atoms, inclusive, which may be a straight chain or branched;
   (c) a cycloalkyl of 3 to 6 carbon atoms, inclusive;
   (d) an alkenyl of 2 to 8 carbon atoms, inclusive, which may be straight chain or branched; or
   (e) $R_aQ_2R_b$, wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

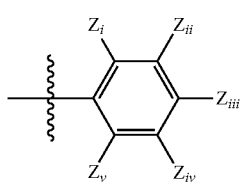

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
   (a) H;
   (b) an alkyl from 1 to 4 carbon atoms, inclusive, straight chain or branched;
wherein T is O or S, and pharmaceutically acceptable salts thereof.

In yet another aspect, lipoxins and lipoxin analogs useful as a BPI inducing agent in the treatment of the maladies, disease states or conditions described throughout the specification has the formula:

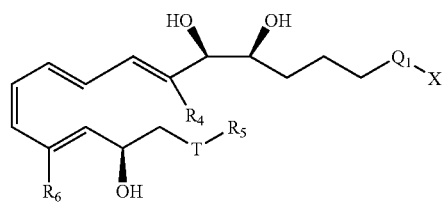

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

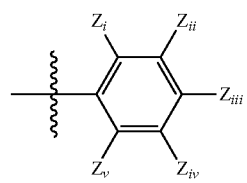

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
   (vii) a detectable label molecule; or
   (viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;
wherein $R_5$ is

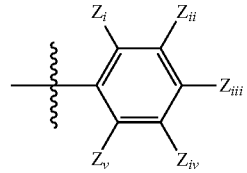

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
   (a) H;
   (b) an alkyl from 1 to 4 carbon atoms, inclusive, straight chain or branched;
wherein T is O or S, and pharmaceutically acceptable salts thereof.

In one aspect, lipoxins and lipoxin analogs useful as a BPI inducing agent in the treatment of the maladies, disease states or conditions described throughout the specification has the formula:

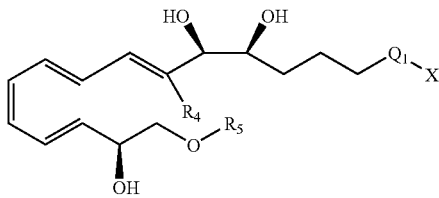

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

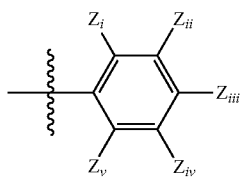

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms,
inclusive;
wherein $R_4$ is
(a) H;
(b) an alkyl of 1 to 6 carbon atoms, inclusive, which may be a straight chain or branched;
wherein $R_5$ is

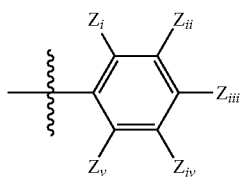

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group; and pharmaceutically acceptable salts thereof.
In preferred embodiments, X is $OR_1$, wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

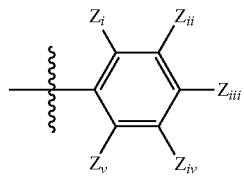

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl. In certain embodiments for $R_5$, para-fluorophenyl and/or unsubstituted phenyl are preferred, e.g., 15-epi-16-(para-fluoro)-phenoxy-LXA$_4$, 16-(para-fluoro)-phenoxy-LXA$_4$, 15-epi-16-phenoxy-LXA$_4$ or 16-phenoxy-LXA$_4$.

In still another aspect, the present invention is directed to pharmaceutical compositions including compounds having the formulae described throughout the specification and a pharmaceutically acceptable carrier. In one embodiment, a preferred compound is

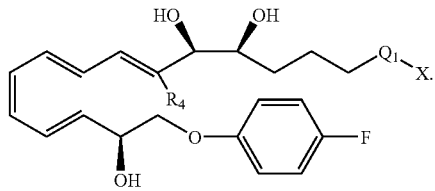

In one embodiment, $Q_1$ is a carbonyl, X is a hydroxyl or an $-OR$, wherein R is an alkyl group, i.e., methyl or ethyl groups, and $R_4$ is a hydrogen atom.

In other embodiments, $Y_1$ is a hydroxyl and the carbon bearing the hydroxyl can have an R or S configuration. In most preferred embodiments, the chiral carbon bearing the hydroxyl group, e.g., $Y_1$, is designated as a 15-epi-lipoxin as is known in the art.

In certain embodiments the chirality of the carbons bearing the $R_2$, $R_3$, $Q_3$ and $Q_4$ groups can each independently be either R or S. In preferred embodiments, $Q_3$ and $Q_4$ have the chiralities shown in above-referenced structures.

In preferred embodiments, $R_4$ is a hydrogen. In other preferred embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

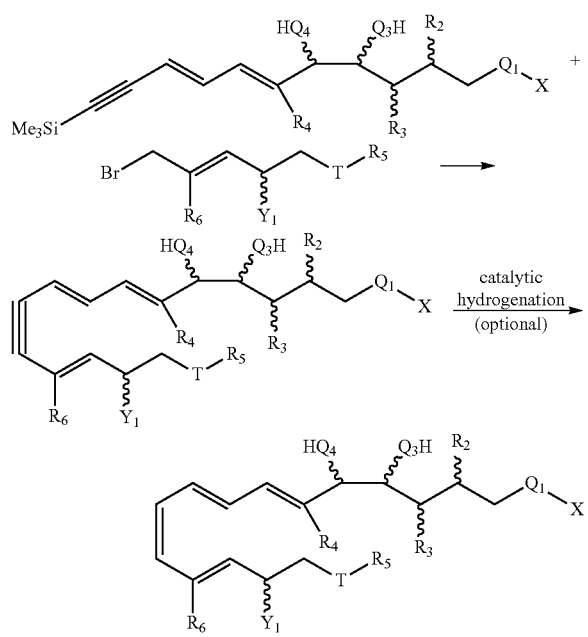

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263. As a consequence, the acetylenic intermediates are also encompassed by the present invention as being useful for the treatments of the various maladies described herein.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as leukotriene C4 and/or leukotriene D4), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. For example, lipoxin $A_4$ analogs have an active region comprising $C_5$-$C_{15}$ of natural lipoxin $A_4$. Similarly, for example, lipoxin $B_4$ analogs have an active region comprising C5-C14 of natural lipoxin B4.

The term "recognition site" or receptor is art-recognized and is intended to refer generally to a functional macromolecule or complex of macromolecules with which certain groups of cellular messengers, such as hormones, leukotrienes, or lipoxins must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lipoxin metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled analog" is further understood to encompass compounds which are labeled with radioactive isotopes, such as but not limited to tritium ($^3H$), deuterium ($^2H$), carbon ($^{14}C$), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native molecule. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin or lipoxin analogs. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo.

The term "subject" is intended to include living organisms susceptible to conditions or diseases caused or contributed bacteria and pathogens as generally disclosed, but not limited to, throughout this specification. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one BPI inducing agent, in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of a BPI inducing agent can be administered as ear drops to treat otitis.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the BPI inducing agent(s) of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the BPI inducing agent may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the BPI inducing agent and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a BPI inducing agent of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Delivery of the BPI inducing agents of the present invention to the lung by way of inhalation is an important method of treating a variety of respiratory conditions (airway inflammation) noted throughout the specification, including such common local conditions as bronchial asthma and chronic obstructive pulmonary disease. The BPI inducing agents can be administered to the lung in the form of an aerosol of particles of respirable size (less than about 10 µm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations should be dispensed in a manner that produces particles or droplets of respirable size.

Once prepared an aerosol formulation is filled into an aerosol canister equipped with a metered dose valve. The formulation is dispensed via an actuator adapted to direct the dose from the valve to the subject.

Formulations of the invention can be prepared by combining (i) at least BPI inducing agent in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components, e.g., ethanol, as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. Conventional neoprene and buna valve rubbers used in metered dose valves for delivering conventional CFC formulations can be used with formulations containing HFC-134a or HFC-227. Other suitable materials include nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Formulations of the invention can be contained in conventional aerosol canisters, coated or uncoated, anodized or unanodized, e.g., those of aluminum, glass, stainless steel, polyethylene terephthalate.

The formulation(s) of the invention can be delivered to the respiratory tract and/or lung by oral inhalation in order to effect bronchodilation or in order to treat a condition susceptible of treatment by inhalation, e.g., asthma, chronic obstructive pulmonary disease, etc. as described throughout the specification.

The formulations of the invention can also be delivered by nasal inhalation as known in the art in order to treat or prevent the respiratory conditions mentioned throughout the specification.

While it is possible for a compound of the present invention to be administered alone, it is preferable to administer the compound as a pharmaceutical composition.

The invention features an article of manufacture that contains packaging material and a BPI inducing formulation contained within the packaging material. This formulation contains an at least one BPI inducing agent and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable BPI inducing agents include, for example, the lipoxin analogs described herein.

More specifically, the invention features an article of manufacture that contains packaging material and at least one BPI inducing agent contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

Methods

Epithelial Cell Culture

T84 and Caco2 intestinal epithelial cells were grown and maintained as confluent monolayers on collagen coated permeable supports as previously described in detail (12), and utilized 6-12 days after plating. The oral epithelial line (KB cells) were grown as described previously (13). Immortalized keratinocytes of oral mucosa origin, generated by ectopic expression of the catalytic subunit of telomerase (hTERT) and were plated and cultured as described previously (14, 15).
Transcriptional Analysis The transcriptional profile of epithelial cells (KB cells) exposed to $LXA_4$ analog (0, 4 or 8 h exposure to 1 µM 15-epi-16-(para-fluoro)-phenoxy-$LXA_4$, ATLa, was assessed in RNA using quantitative genechip microarrays (Affymetrix, Inc.) (16). RT-PCR analysis of mRNA levels was performed using DNAse treated total RNA as previously described (17). Briefly, single stranded cDNA was synthesized from 1 µg RNA (DNA Polymerase High Fidelity PCR System, Gibco Life Technologies, Grand Island, N.Y.). The PCR reaction for human BPI contained 1 µM each of the sense primer (5'-GCA CCT GTT CCT GAT GGG-3' (SEQ ID NO:1)) and the antisense primer (5'-AGC ACA AAT GGA AAT TTC TTG-3' (SEQ ID NO:2)) in a total volume of 50 µl resulting in a 255 bp fragment. The PCR reaction for human ICAM-1 contained 1 µM each of the sense primer (5'-CAC AGT CAC CTA TGG CAA CG-3' (SEQ ID NO:3)) and the antisense primer (5'-TTC TTG ATC TTC CGC TGG C-3' (SEQ ID NO:4)) in a total volume of 50 µl resulting in a 750 bp fragment. Products for PCR reactions were then visualized on a 1% agarose gel containing 5 µg/ml of ethidium bromide. Human β-actin expression was examined in identical conditions as an internal control [sense primer (5'-TGA CGG GGT CAC CCA CAC TGT GCC CAT CTA-3' (SEQ ID NO:5)) and antisense primer (5'-CTA GAA GCA TTT GCG GTG GAC GAT GGA GGG-3' (SEQ ID NO:6))] revealing a 661 bp amplified fragment.
Confocal Laser Scanning Microscopy OKF6 or Caco2 cells were grown to confluence on acid washed 12 mm glass coverslips. Monolayers were exposed to indicated experimental conditions, washed once in phosphate buffered saline, and fixed for 10 minutes at room temperature in 1% paraformaldehyde in cacodylate buffer (0.1M sodium cacodylate; pH 7.4, 0.72% sucrose). After washing twice with PBS, the cells were incubated for 1 hour with rabbit polyclonal BPI antisera (1:300 dilution) or control sera (equivalent dilution depleted of specific antibody through 3 consecutive adsorptions with sepharose beads covalently linked to rBPI via cyanogens bromide coupling, kit from Pierce Chemical Co., Rockford, Ill.). After washing, the monolayers were incubated with goat anti-rabbit Oregon Green (1 µg/ml, Molecular Probes, Eugene, Oreg.). Cells were imaged on a BioRad MRC-600 confocal fluorescence microscope.
Immunoprecipitation and Western Blotting Epithelial cells were grown to confluence on 45 $cm^2$ permeable supports, and exposed to ATLa or vehicle (0.01% EtOH), as indicated. Cells were washed extensively in HBSS, cooled to 4° C., and extracellular proteins were biotinylated (1 mM NHS-biotin (Pierce Chemical Co., Rockford, Ill.) in HBSS) as previously described (18). Plasma membranes were isolated using nitrogen cavitation (200 psi, 8 min., 4° C.) as previously described (18). Recombinant human BPI (100 ng/ml, was directly biotinylated and excess biotin was removed by multiple washes on a 5 kD cut-off membrane filter (Amicon, Beverly Mass.). Fractions were pre-cleared with 50 µl pre-equilibrated protein-G sepharose (Pharmacia, Uppsala Sweden). Immunoprecipitation of BPI was performed with goat polyclonal anti-BPI followed by addition of 50 µl pre-equilibrated protein-G sepharose and overnight incubation. Washed immunoprecipitates were boiled in non-reducing sample buffer (2.5% SDS, 0.38 M Tris pH 6.8, 20% glycerol, and 0.1% bromophenol blue), resolved by non-reducing SDS-PAGE (18% polyacrylamide gel), transferred to nitrocellulose, and blocked overnight in blocking buffer. Biotinylated proteins were labeled with streptavidin-peroxidase (Pierce Chemical Co., Rockford, Ill.) and visualized by enhanced chemiluminescence (ECL; Amersham, Arlington Heights, Ill.).
Cell Surface Immunoassay ICAM-1 cell surface expression was quantified using a cell surface ELISA, as described before (19). Epithelial cells were grown and assayed for antibody binding following exposure to indicated concentrations of LPS (from *Salmonella minnesota* Re595, List Biological Laboratories, Inc, Cambell, Calif.) in the presence of 5% heat inactivated normal human serum. Following such exposure, cells were washed with HBSS (Sigma, St. Louis, Mo.), blocked with media for 30 min at 4° C. Anti-ICAM-1 mAb (clone P2A4 (20) obtained from the Developmental Studies Hybridoma Bank, Iowa City, Iowa, used as undiluted cell culture supernatant) was added and allowed to incubate for 2 h at 4° C. After washing with HBSS, a peroxidase conjugated sheep anti-mouse secondary antibody (Cappel, West Chester, Pa.) was added. Secondary antibody (1:1000 final dilution) was diluted in media containing 10% fetal bovine serum. After washing, plates were developed by addition of peroxidase substrate [2,2'-azino-bis(3-ethylbenzthiazoline-6-sulfonic acid), 1 mM final concentration, Sigma] and read on a microtiter plate spectrophotometer at 405 nm (Molecular Devices). Controls consisted of media only and secondary antibody only. In subsets of experiments, a polyclonal anti-BPI antisera with demonstrated BPI neutralizing activity (21) (goat anti-human, used at 1:300 in HBSS) or normal goat serum (Invitrogen, Carlsbad, Calif., 1:300 in HBSS), as indicated, were added prior to incubation with endotoxin. Data are presented as the mean±s.e.m. optical density (OD) at 405 nm (background subtracted).
Bacterial Killing Assays

*Salmonella typhimurium* (strain 14028 from American Type Culture Collection, Rockville, Md.) were cultured and grown in Luria broth as previously described (22). In subsets of experiments, *Enterococcus faecalis* (strain PCI 1326 from American Type Culture Collection, Rockville, Md.) were cultured as previously described (23). Caco2 epithelial cells were grown to confluence of 60 mm petri dishes and exposed to indicated experimental conditions. Cells were washed once with HBSS, and washed bacteria were added to epithelial monolayers at a ratio of 50 bacteria per adherent epithelial cell. Incubations were allowed to proceed for 90 minutes or as indicated on a rotating platform. Parallel samples omitting epithelial cells were used as controls. Following incubation, supernatants were collected and epithelial cells were hypotonically lysed with 1 ml ice cold water. Bacteria were pelleted, dilutions of both pellets and supernatants were plated, incubated overnight at 37° C., and colony counts were performed. In subsets of experiments, anti-BPI antisera (1:300 in HBSS) or anti-BPI antisera pre-adsorbed with rBPI (1:300 in HBSS), as indicated, were added 30 minutes prior to incubation with bacteria. Data are presented as the mean±S.E.M. CFU.

Localization of BPI in Human Tissue

Normal human esophageal or colonic specimens were obtained under an approved human institutional review board protocol. Sections were fixed in 10% buffered formalin, paraffin embedded, and sectioned using standard methods. Antigen retrieval was performed in a pressure cooker with EDTA Decloaker solution, pH 8.0 (Zymed Labs, San Francisco, Calif.) according to manufacturers recommendations. Sections were stained with rabbit polyclonal BPI antisera (1:100) and peroxidase-coupled secondary antibody (1 µg/ml, Zymed Labs, San Francisco, Calif.) and visualized by peroxidase method according to manufacturers recommendations (Vectastain, Vector Laboratories, Burlingame, Calif.). Control sections were incubated with BPI pre-adsorbed Ab (1:100 dilution), as indicated. Sections were visualized with a Nikon E600 microscope at 200× magnification.

Data Analysis

BPI bioactivity results were compared by two-factor analysis of variance (ANOVA) or by Student's t-Test, where appropriate. Values are expressed as the mean and S.E.M. of n monolayers from at least 3 separate experiments.

Results

Epithelial Cells Express BPI and Such Expression is Regulated by Lipoxins

Lipoxins possess potent anti-inflammatory properties for mucosal inflammation (3). Epithelial cells of diverse origin express functional receptors for lipoxins, however, little is known about downstream transcriptional pathways elicited by ligation of the lipoxin receptor. Thus, a transcriptional profiling approach (16) was utilized to identify potential lipoxin-regulated gene expression in model epithelia (KB cells). This analysis revealed that 97 out of 7129 genes screened (1.4%) were induced by greater than 3-fold by ATLa and 36 of 7129 screened (0.5%) were decreased by exposure to ATLa. This analysis identified the expression and upregulation of BPI by ATLa in epithelial cells, providing the interesting possibility that this molecule may provide anti-infective qualities for the epithelium. Indeed, basal expression of the BPI mRNA comparable to glyceraldehyde phosphate dehydrogenase and a dominant induction of BPI by ATLa (3.2- and 2.9-fold increase over control at 4 and 8 hrs exposure to ATLa, respectively, FIG. 1A). RT-PCR analysis was employed to verify these microarray results at the RNA level. As shown in FIG. 1B, semi-quantitative RT-PCR revealed that, relative to β-actin, ATLa (1 µM exposure, 8 h) induced a prominent induction of BPI compared to vehicle control (maximal increase of 4.3-fold increase by densitometry). Dose response analysis revealed an approximate $EC_{50}$ of 50 nM (FIG. 1C). Epithelial exposure to similar concentrations of 15-deoxy-$LXA_4$, a lipoxin analog lacking demonstrable bioactivity (4), resulted in no induction of BPI at the mRNA level (data not shown).

As shown in FIG. 1D-F, similar analysis utilizing RNA (26 cycles of PCR) derived from epithelial cells other than KB cells (OKF6, T84 and Caco2 cells) revealed a prominent pattern of time-dependent BPI induction by ATLa (1 µM) relative to β-actin. Importantly, such results were not universal for all cell types, since no detectable BPI transcript was evident with as many as 35 cycles of PCR in RNA derived from human dermal microvascular endothelial cells (data not shown), suggesting that these findings may be relatively specific for epithelia. Moreover, consistent with previous studies indicating that lipoxin signaling is a G protein coupled event (24), Caco2 pre-exposure to pertussis toxin (1 µM, 30 min) resulted in a 65% decrease in BPI induction by ATLa (1 µM, 18 h, data not shown). Taken together, these findings indicate specific transcriptional activation of BPI by ATLa.

Localization of BPI Protein to the Epithelial Cell Surface

Figure 2:
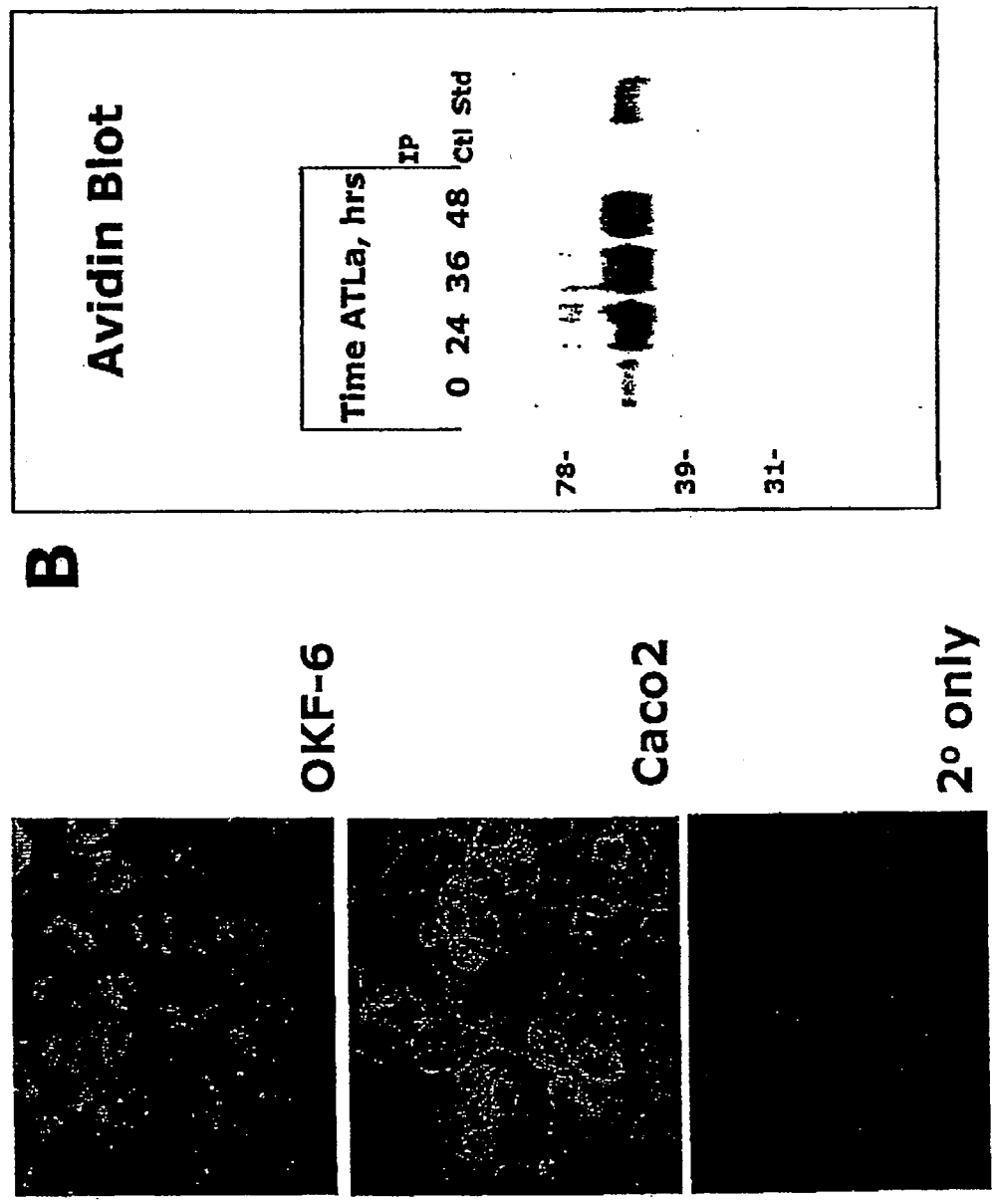
FIG. 2 depicts localization of BPI to the cell surface. In panel A, BPI was localized by confocal microscopy in non-permeabilized OKF6 or Caco2 cells, as indicated. Shown in FIG. 2 are confocal sections through the mid-zone, sub-junctional portion of epithelial monolayers. Also shown is a control section omitting the primary Ab. Representative experiment from n=2. In panel B, T84 cells were pre-exposed to ATLa (1 µM) for indicated periods of time. Cell surface proteins were non-specifically labeled with biotin, BPI was immunoprecipitated from cell lysates, resolved by SDS-PAGE and western blots were probed with avidin peroxidase. Also shown is the immunoprecipitation control (omission of primary antibody) as well as a biotinylated BPI standard. Representative experiment from n=3.

Previous studies have indicated that BPI can exist as a granule-bound protein or as a surface-associated protein on neutrophils (25). Initial attempts to detect soluble BPI using a sulfuric acid extraction known to release granule-bound BPI from neutrophils (26) (ELISA and western blot of soluble epithelial supernatants) revealed undetectable levels of BPI (sensitivity <100 pg/ml, data not shown). Thus, in an attempt to localize expression patterns of epithelial-expressed BPI, confocal microscopy was utilized on non-permeabilized epithelia. As shown in FIG. 2A, BPI was expressed in a surface-bound form on both OKF-6 cells as well as Caco2 cells. The expression pattern was dominant on the lateral membrane surface, with some evidence for a punctuate pattern in OKF6 cells.

As biochemical verification of these observations, and to examine whether ATLa (1 µM) induces BPI at the protein level, immunoprecipitation of biotinylated plasma membrane protein followed by avidin blot was utilized. This approach allows for detection of surface membrane proteins derived from intact epithelial cells (27). As depicted in FIG. 2B, a time course of ATLa (1 µM) exposure was performed and revealed a dominant induction (maximal 12.5-fold increase at 36 h by densitometry) of a ~55 kDa surface protein consistent with BPI (biotinylated recombinant BPI is shown for comparative purposes). Controls incorporating a polyclonal antibody directed against a soluble epithelial protein (the chemokine IL-8) revealed no detectable protein at this level. Such analysis indicates the likelihood that BPI exists predominantly as a membrane-bound protein on the surface of epithelial cells and that such expression is regulated by ATLa.

Figure 3:
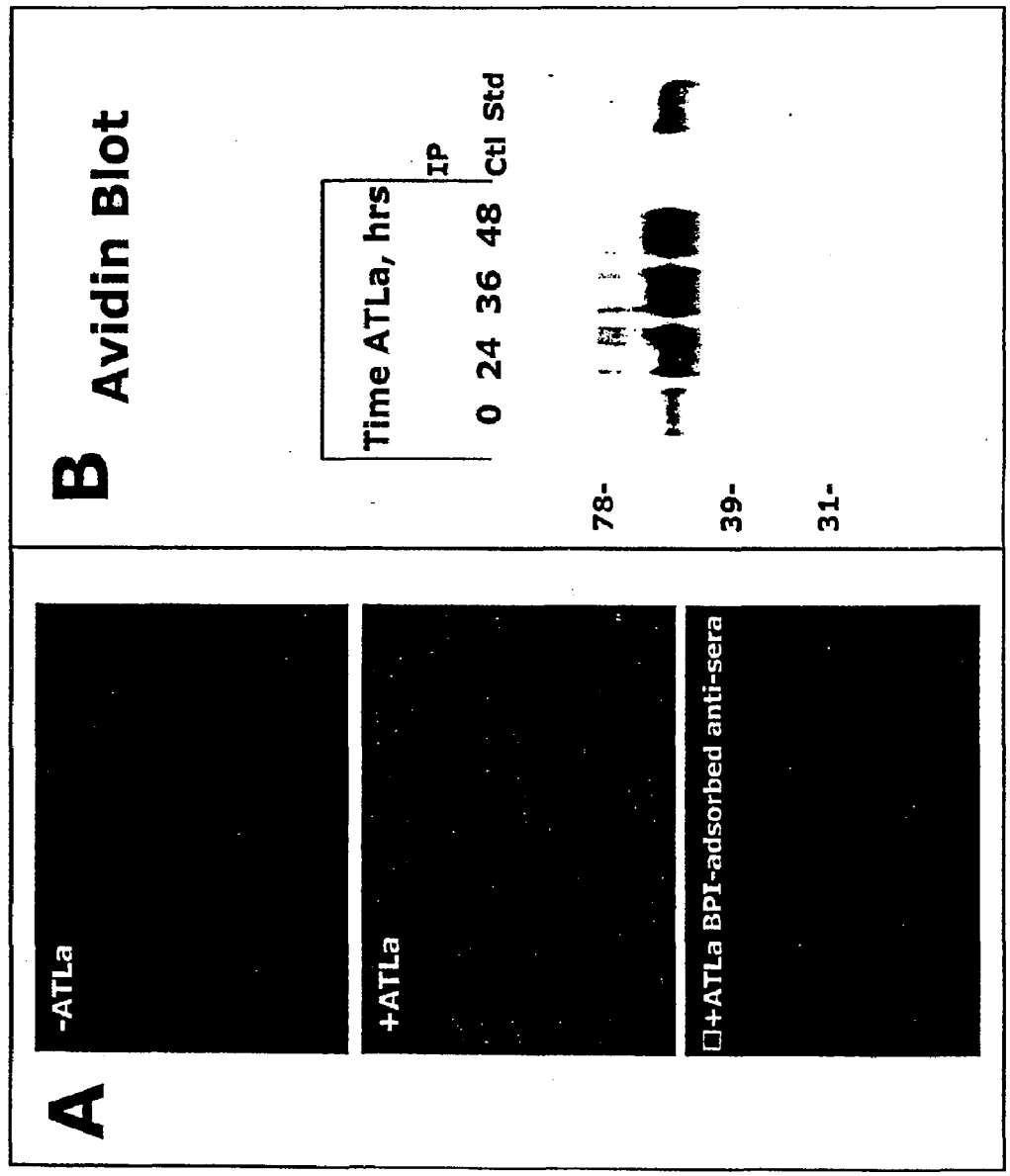
FIG. 3 also depicts localization of BPI to the cell surface. In panel A, BPI was localized by confocal microscopy in non-permeabilized Caco2 cells exposed to vehicle (top panel) or ATLa (1 µM, 24 hours, middle and bottom panel). In the bottom panel, BPI adsorbed antisera was used as a control. Shown in FIG. 2 are confocal sections through the mid-zone, sub-junctional portion of epithelial monolayers. Representative experiment from n=2. In panel B, T84 cells were pre-exposed to ATLa (1 µM) for indicated periods of time. Cell surface proteins were non-specifically labeled with biotin, BPI was immunoprecipitated from cell lysates, resolved by SDS-PAGE and western blots were probed with avidin peroxidase. Also shown is the immunoprecipitation control (omission of primary antibody) as well as a biotinylated BPI standard. Representative experiment from n=3.

As shown in FIG. 3A, BPI was expressed in a surface-bound form on Caco2 cells, with increased expression associated with ATLa exposure (1 µM for 24 hr, see FIG. 3A). As a control for specificity, parallel samples exposed to ATLa (1 µM for 24 hr) were incubated with BPI pre-adsorbed antisera, and revealed a nearly complete loss of surface staining.

Endotoxin Neutralization by Epithelial BPI

Figure 4:
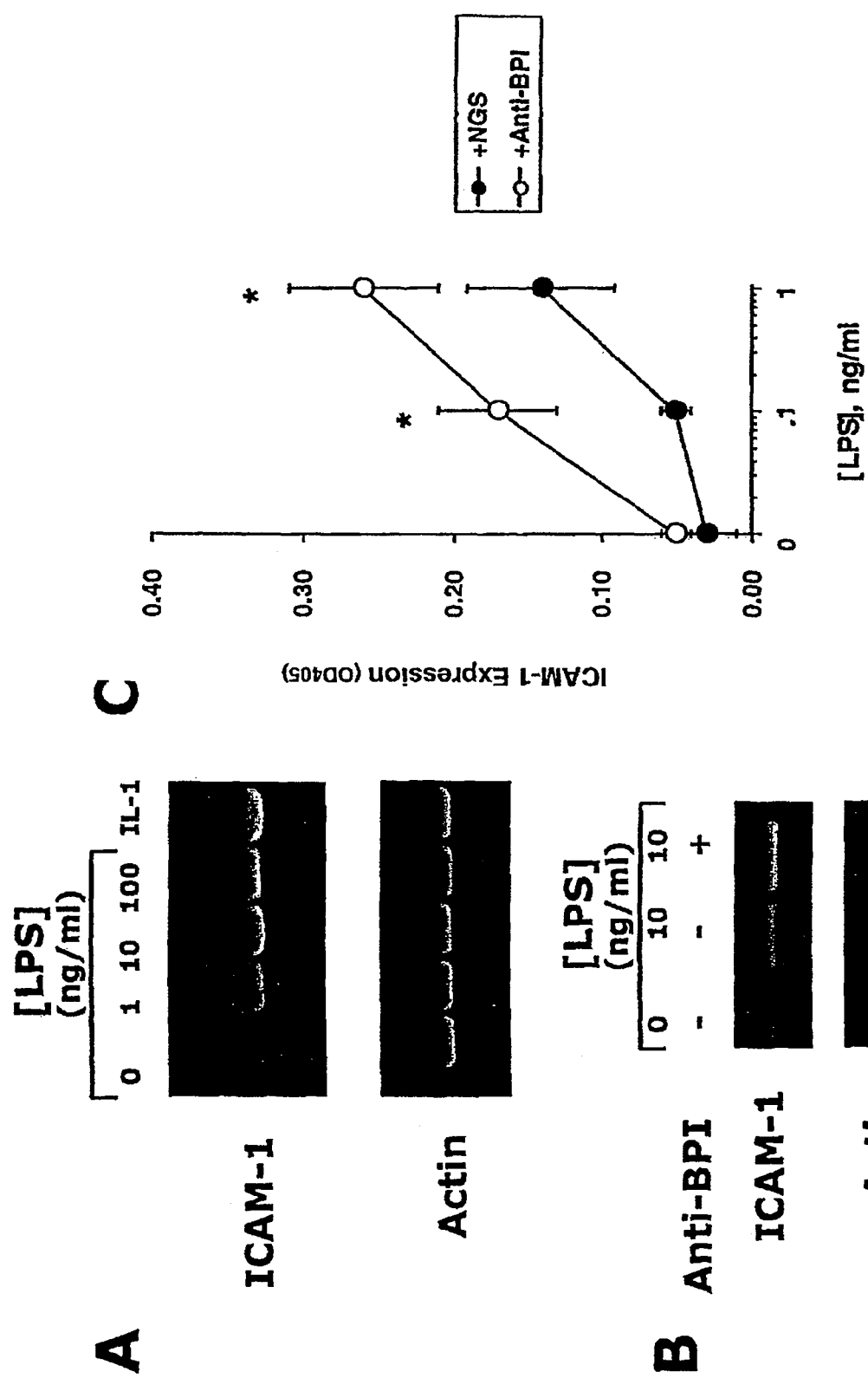
FIG. 4 depicts BPI functionally regulating epithelial endotoxin responses. In panel A, transcriptional induction of ICAM-1 was examined in KB cells in response to indicated concentrations of endotoxin (LPS) in the presence of NHS (5% v/v) or IL-1 (10 ng/ml) for 8 hr. Total RNA was isolated and used to assess ICAM-1 transcripts by RT-PCR. β actin transcript was used as an internal standard. In panel B, endotoxin-induced ICAM-1 expression was examined in the presence polyclonal anti-BPI (+) or in the presence of NGS (−). β actin transcript was used as an internal standard. In panel C, KB cells were preexposed to ATLa (1 µM, 8 hr) and cell surface ELISA was used to screen ICAM-1 protein induction by endotoxin/5% NHS (additional 24 hr) in the presence of anti-BPI or control NGS. Single asterisk (*) indicates significantly different from NGS, $p<0.025$).

We next extended these studies to examine the functional activity of BPI on the epithelial surface. Previous studies have indicated that BPI possesses not only bactericidal, but also endotoxin-neutralizing activity (7). Since epithelial cells have been previously shown to transcriptionally respond to endotoxin in the presence of serum (28), it was first determined whether endotoxin might induce ICAM-1, an endotoxin-responsive marker which functions as a leukocyte adhesion molecule (29) in RNA derived from KB cells. As shown in FIG. 4A, addition of endotoxin to KB cells in the presence of 5% heat inactivated normal human serum induced a concentration-dependent induction of ICAM-1 mRNA, comparable to a known ICAM-1 agonist (interleukin-1, 10 ng/ml).

Having shown that epithelial cells respond to endotoxin, it was next determined whether inhibition of basally expressed BPI (i.e. in the absence of $LXA_4$) might function to enhance endotoxin-mediated induction of ICAM-1 surface protein. To this end, epithelial cells were pre-exposed to anti-BPI or control NGS and subsequently activated with a combination of endotoxin (concentration range 0-1 ng/ml) in the presence of 5% normal human serum. Transcriptional analysis of the ICAM-1 response to endotoxin is shown in FIG. 4B. The addition of anti-BPI serum significantly increased endotoxin-induced ICAM-1 transcript (2.3±0.45-fold, n=3, p<0.01 compared to NGS) suggesting that BPI provides an endotoxin-neutralizing function for epithelial cells. Similar results were found using Caco2 cells (2.0±0.61-fold increase with anti-BPI compared to NGS, p<0.05). Moreover, as shown in FIG. 4C, anti-BPI shifted the endotoxin dose response curve for ICAM-1 induction to the left compared to control NGS, with significant differences evident at 0.1 and 1 ng/ml (both p<0.025 by ANOVA). When higher concentrations of endotoxin were used, the influence of anti-BPI was less apparent (data not shown). Such data indicate that surface expressed BPI might normally function to dampen epithelial endotoxin responses.

Role of Surface BPI in Bacterial Killing

Figure 5:
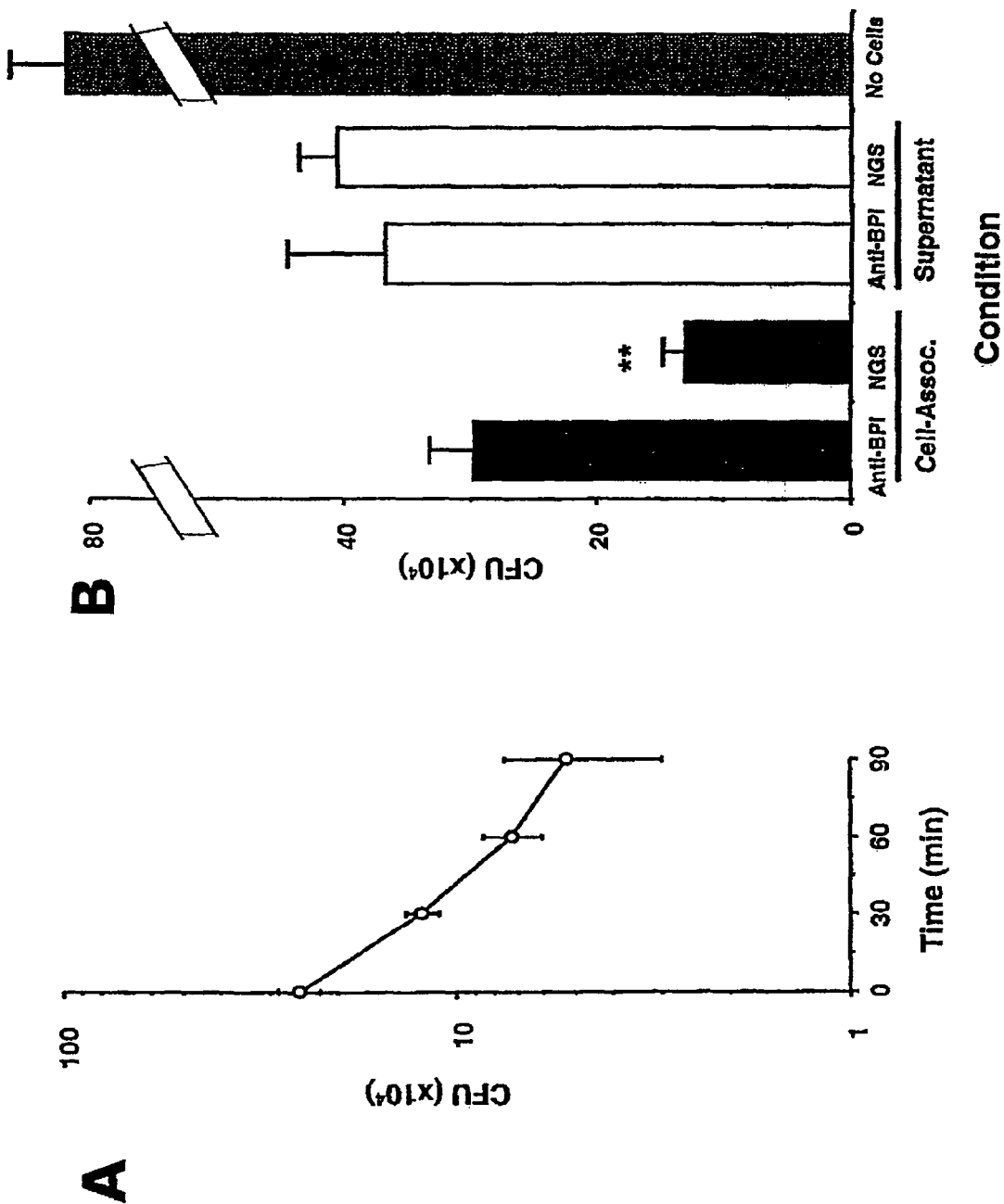
FIG. 5 depicts the role of epithelial BPI in bacterial killing. In panel A, adherent Caco2 cells were incubated with *S. typhimurium* at a ratio of 50 bacteria per epithelial cell and examined for killing over a 90 min period as described in *Materials and Methods*. Shown in FIG. 4 are pooled results from three experiments. In panel B, the role of BPI in Caco2 killing of *S. typhimurium* over a 60 min period was assessed by incubation of cells (Cell Assoc.) or supernatants with anti-BPI or NGS. The bacterial control omitting epithelial cells is also shown. Double asterix (**) indicates significantly different from anti-BPI, $p<0.01$).

It was next determined whether intact, adherent epithelial cells kill a BPI-sensitive bacteria. Confluent Caco2 epithelial cells were exposed to *S. typhimurium* and examined for bacterial killing in standard colony-forming unit (CFU) analysis using adherent epithelial cells. As shown in FIG. 5A, such analysis revealed a nearly 1-log order reduction in CFU over a 90 min period (83±11% killing, p<0.025 by ANOVA). To define the role of BPI under such circumstances, similar studies were performed on adherent epithelial cells or soluble supernatants pre-exposed to anti-BPI or control NGS. As shown in FIG. 5B, anti-BPI exposure to adherent epithelia, but not soluble supernatants, significantly inhibited bacterial killing compared to control NGS (p<0.01). Parallel experiments assessing epithelial killing of a Gram-positive bacterium (*Enterococcus faecalis*) that is not sensitive to BPI indicated a smaller degree of killing (0.3±0.05-log order reduction in CFU over 90 min) but no influence of anti-BPI on such killing (5.5±2.1% decrease in killing, p=not significant).

Figure 6:
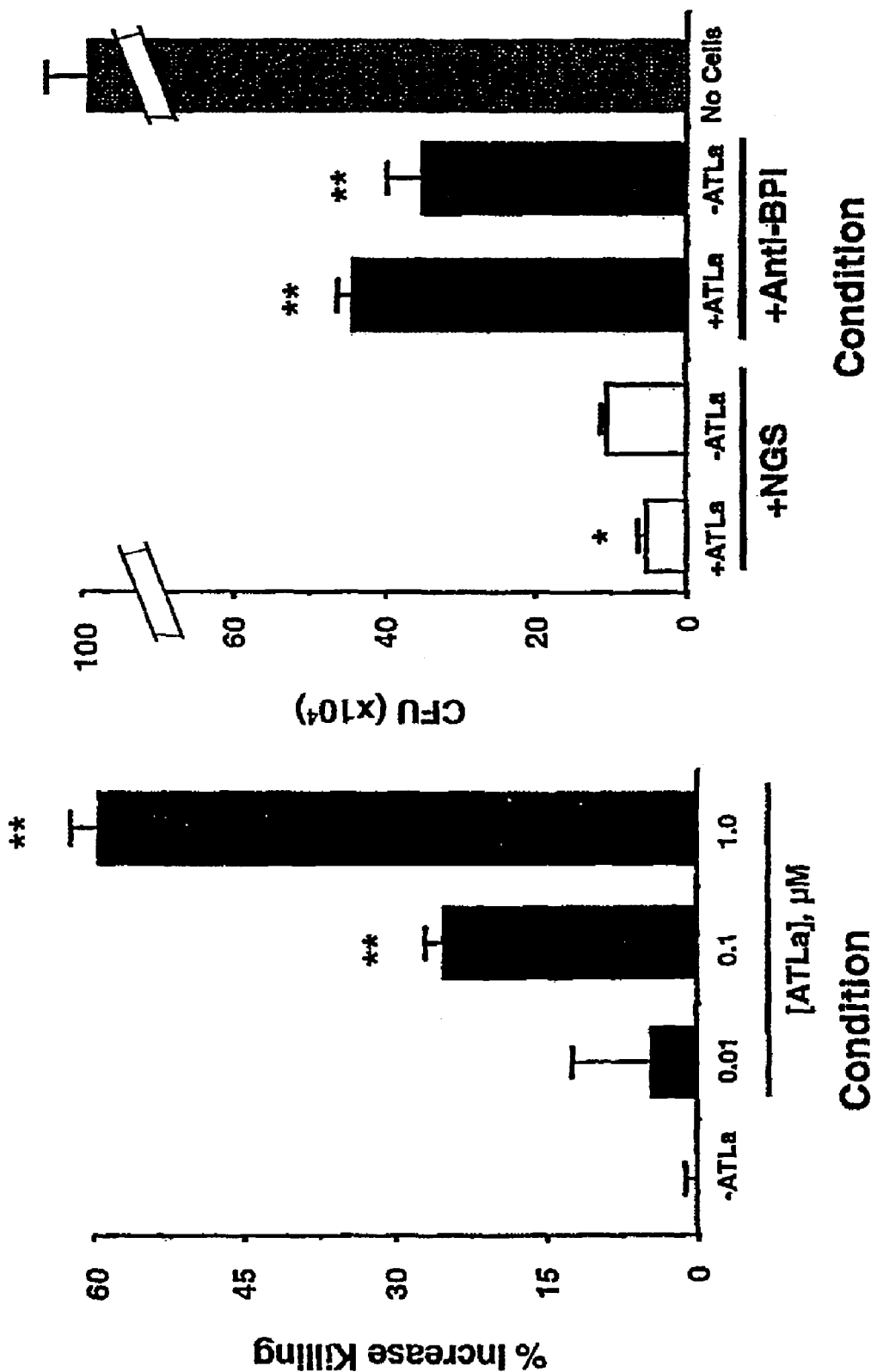
FIG. 6 demonstrates that ATLa enhances BPI-dependent bacterial killing. Adherent Caco2 cells were incubated with vehicle or indicated concentrations of ATLa (24 hr) and the role of BPI in Caco2 killing of *S. typhimurium* over a 60 min period was assessed. Panel A demonstrates concentration dependent increases in bacterial killing with prior exposure to ATLa. In panel B, the relative contribution of BPI was examined by incubation anti-BPI or NGS. The bacterial control omitting epithelial cells is also shown. Shown here are pooled results from three experiments. Single asterisk (*) indicates significantly increased killing compared to vehicle (p<0.025) and double asterix (**) indicates significantly different from NGS control (p<0.01).

These studies were extended to determine whether BPI induction by ATLa might functionally enhance killing of BPI-sensitive bacteria. As shown in FIG. 6A, epithelial pre-exposure to ATLa increased bacterial killing in a concentration-dependent fashion (p<0.025 by ANOVA), with a nearly 60% increase in killing at 1 µM ATLa. To determine the relative contribution of BPI to such activity, Caco2 cells were exposed conditions which induce surface BPI (1 µM ATLa for 24 h) and analyzed for bactericidal activity as above. As shown in FIG. 6B, this component of increased bacterial killing was attributable to induction of BPI since the presence of anti-BPI inhibited such bacterial killing (p<0.01 compared to control NGS). Such observations indicate that surface BPI functions in bacterial killing and that such responses are significantly regulated by anti-inflammatory lipid mediators (i.e. ATLa).

Figure 7:
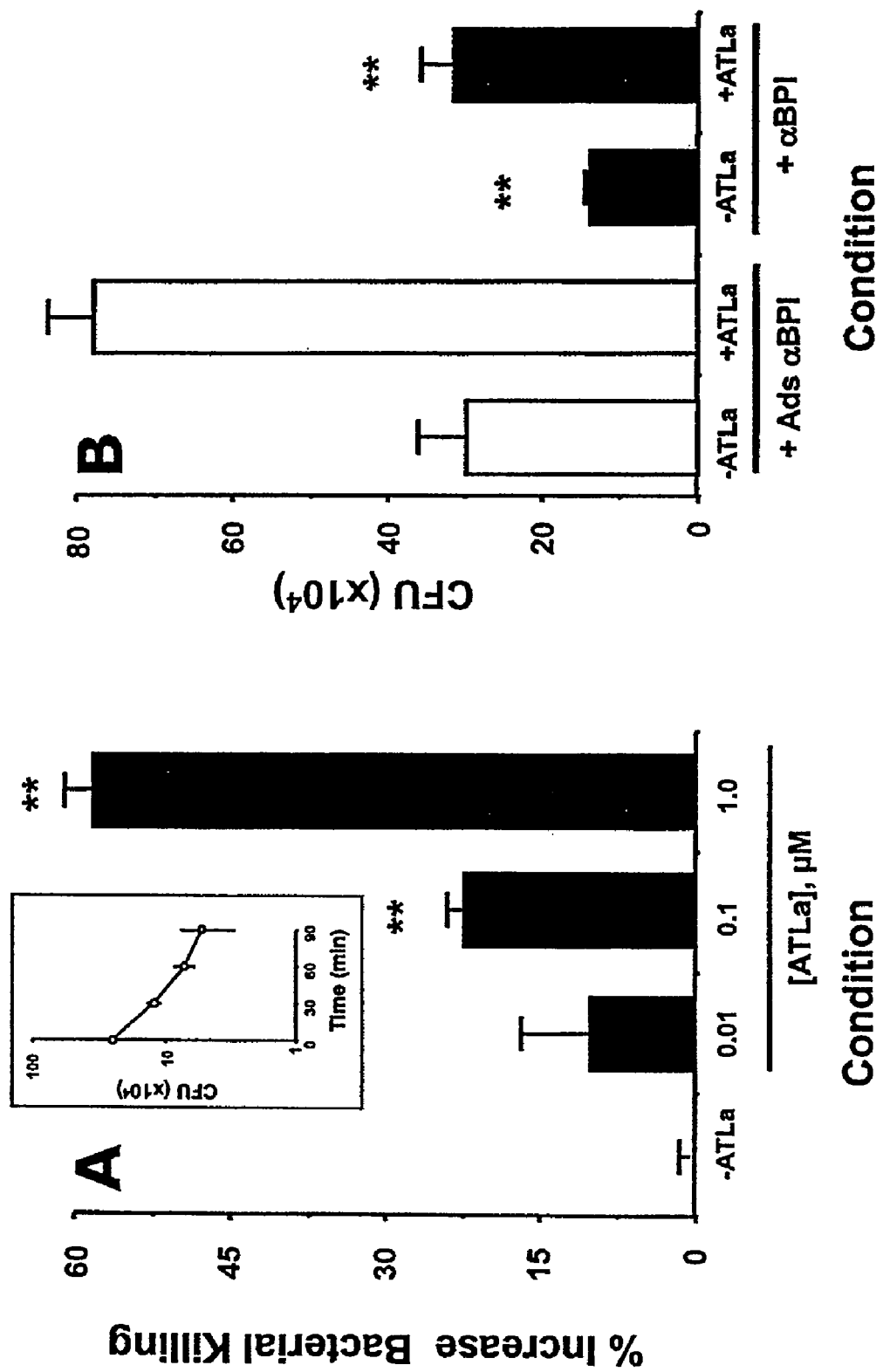
FIG. 7 also demonstrates that ATLa enhances BPI-dependent bacterial killing. Adherent Caco2 cells were incubated with vehicle or indicated concentrations of ATLa (24 hr) and the role of BPI in Caco2 killing of *S. typhimurium* over a 60 min period was assessed. Panel A demonstrates concentration dependent increases in bacterial killing with prior exposure to ATLa. The inset of panel A represents a killing curve in the absence of ATLa. In panel B, the relative contribution of BPI was examined by incubation anti-BPI or control antisera pre-adsorbed with rBPI. Shown here are pooled results from three experiments. Double asterisk (**) indicates significantly different from control condition (p<0.01).
Figure 8:
FIG. 8 depicts staining of normal human intestinal (panel A) and normal human esophagus (panel B) tissue for BPI. Arrows indicate predominant epithelial staining.
Figure 8:
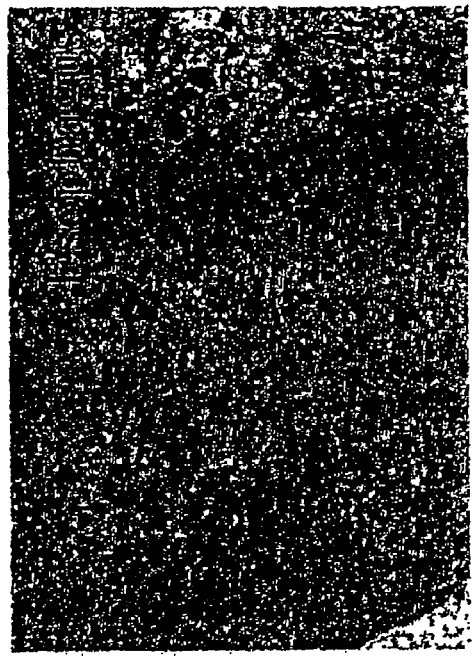

As shown in FIG. 7B, a significant component of increased bacterial killing was attributable to induction of BPI, since the addition of anti-BPI inhibited such bacterial killing (p<0.01 compared to anti-BPI adsorbed with rBPI). These results were not explained by bactericidal activity or non-specific agglutination by either ATLa or anti-BPI (based on direct incubation of ATLa or anti-BPI with bacteria and colony counts, data not shown). Parallel experiments assessing epithelial killing of a Gram-positive bacterium (*Enterococcus faecalis*) that is not sensitive to BPI indicated a smaller degree of killing (0.3±0.05-log order reduction in CFU over 90 min) but no influence of anti-BPI on such killing (5.5±2.1% decrease in killing, p=not significant). Such data indicate that BPI contributes to bacterial killing by epithelial cells and that ATLa-induced BPI enhances this functional response.

Localization of BPI in Native Mucosal Tissue

Figure 9:
FIG. 9 depicts localization of epithelial BPI in human mucosal tissues. Normal human esophageal (panels A and B) or colon (panels C and D) specimens were obtained, fixed in 10% buffered formalin, paraffin embedded, and sectioned. Following antigen retrieval, sections were stained with rabbit polyclonal BPI antisera (panels A and C) or control sera (BPI pre-adsorbed Ab, panels B and D), followed by peroxidase-coupled secondary antibody, and then visualized by peroxidase method. Sections were visualized at 200× magnification. Arrows indicate areas of dominant BPI localization.

Further studies examined whether native tissues express BPI and whether such expression localizes to the epithelium. Since the findings above (FIG. 1) suggest that both columnar (e.g. T84 and Caco2 cells) and squamous epithelia (e.g. KB and OKF6 cells) express BPI, squamous and columnar epithelial bearing tissues (esophagus and colon, respectively) were examined. As shown in FIG. 9, analysis of normal human esophagus (panel A) and colon (panel C) sections revealed dominant localization of BPI to the epithelium. In the case of esophageal tissue, BPI was most strongly expressed at the transition zone between epithelia and the lamina propria, with graded decreasing expression toward surface epithelia. In the colon, BPI was expressed dominantly in crypt and villus epithelia, with less expression along the crypt-villus axis. In both the esophagus and colon, localization with pre-adsorbed anti-BPI revealed no specific signal (panels B and D, respectively). These findings in native human tissue demonstrate that BPI is expressed in vivo.

Discussion

Mucosal epithelial cells provide a first line of defense against bacterial invasion and infection. While much is known regarding innate mechanisms of bacterial clearance by leukocytes, it is only recently appreciated that epithelial cells might also function in a similar capacity (8, 30). In these studies, the broad regulation of epithelial genes by ATLa was explored, and in the course of these experiments, identified previously unappreciated expression of functional epithelial BPI. Such expression was localized to the membrane surface in cell lines and in diverse mucosal tissues in situ, and data are provided that epithelial-associated BPI serves to both inhibit endotoxin signaling as well as provide a pathway to dampen bacterial infection.

Mucosal epithelial cells harbor a number of antimicrobial factors which form a biochemical barrier to microbial colonization (8, 30, 31). Numerous studies have indicated that these antimicrobial factors are critical to maintenance of host-microbe homeostasis at the mucosal surface (8, 30). Studies in the present invention identified the expression of BPI mRNA in epithelial cells, and extensions of these findings revealed broad expression on epithelia of diverse origin. Without exception, BPI expression has been described only in cells of myeloid lineage (8). Two conceptual points exemplify the potential importance of BPI expression on mucosal epithelia. First, epithelia provide the initiation point for host-microbial interactions. While microbial flora are necessary and beneficial to the host, some degree of selectivity is also prerequisite for homeostasis. Epithelial-expressed BPI could provide such a role. BPI is remarkable for its potent (nanomolar) and selective bioactivity against gram-negative bacterial species (9). Moreover, the finding that functional BPI is expressed on the epithelial surface, and not in the soluble milieu, could provide an additional degree of selectivity for invasive/host-interactive pathogens. Second, a basic feature of many mucosal surfaces is the presence of high concentrations of endotoxin. Previous work has indicated that under appropriate conditions, epithelial cells can respond to endotoxin (28), and recent studies have clearly defined the existence of LPS receptors (e.g. CD14 and TLR4) on epithelial surfaces (32), the latter of which may be differentially regulated in selective mucosal diseases (33). For this reason, endogenous mechanism(s) likely exist to diminish aberrant activation of epithelial cells. The present invention provides that BPI expression in epithelial cell lines and in native epithelia provides an innate dampening mechanism against endotoxin by effectively competing for the binding of endotoxin, and as such, preventing endotoxin binding to such pro-inflammatory receptors. Indeed, endotoxin activation of epithelia (i.e. ICAM-1 induction) was significantly enhanced by the addition of functionally inhibitory anti-BPI sera, suggesting a protective role for BPI in mucosal endotoxin homeostasis. Of note, at higher concentrations of endotoxin (e.g. >50 ng/ml), the influence of epithelial expressed BPI was less obvious, suggesting that the relative concentration of BPI and/or the LPS affinity of BPI compared to LPS receptors (CD14/Toll-like receptors) may favor activation at high LPS concentrations. Taken together, epithelial BPI contributes to the innate biochemical barrier characteristic of mucosal surfaces, but also provides a degree of selectivity necessary for effective host responses.

Lipoxins have been implicated in a number of anti-inflammatory pathways. Here, the present invention demonstrates that ATLa, a stable analog of aspirin-triggered lipoxin (5), potently induces transcriptional activation of BPI. Little is known about transcriptional pathways of BPI induction, and to date, the BPI promoter has not been characterized. Lipoxins have been widely studied as anti-inflammatory agents and have been demonstrated to inhibit PMN transmigration across both endothelia and epithelia (4, 24), block PMN diapedesis within the microcirculation (34) and may initiate the resolution phase of ongoing inflammation (35). Noteworthy is the finding that lipoxins are potent inhibitors of bacterial-induced inflammation in the murine air pouch model (36). In this model, lipoxins inhibited expression of COX-2, an endotoxin-stimulated gene product (37). Thus, lipoxins may dampen inflammatory processes by controlling bacterial overgrowth and/or inhibit endotoxin activation via transcriptional induction of BPI.

The present invention provides implications to a number of mucosal disease processes. Infectious agents have been implicated as important etiologic agents in diseases ranging from periodontal disease (38) to inflammatory bowel disease (39). Attempts to attribute individual diseases to single specific bacterial strains have failed, and thus, attention has turned toward understanding bacterial-host interactions. BPI has become an important expression marker for a number of diseases. For example, high levels of neutrophil-associated BPI are found in the colonic mucosa of patients with ulcerative colitis (40, 41), and auto-antibodies directed against BPI are proposed seromarkers for the inflammatory bowel diseases (42). Moreover, BPI congeners are currently being evaluated as novel therapies for diseases in which endotoxin is thought to play a role (43), including Crohn's disease (44). The present invention provides further support for the notion that BPI plays important anti-infective roles in the gastrointestinal tract, particularly as a molecular shield that dampens the inflammatory influence of endotoxin.

In summary, these results contribute to the present knowledge of mucosal defense mechanisms, and define a previously unappreciated expression of BPI on the surface of alimentary tract epithelia, including those derived from the oral cavity, esophagus and intestine. Moreover, regulated expression of BPI by ATLa provides additional clues to the potent nature of these anti-inflammatory agents and provides for the possible therapeutic induction of BPI in treatment of mucosal infections.

REFERENCES

1. Serhan, C. N., Haeggstrom, J. Z., Leslie, C. C., (1996) *FASEB J.* 10, 1147-1158.
1.A Ganz, T., and J. Weiss. (1997) Antimicrobial peptides of phagocytes and epithelia. Semin Hematol 34, 343-54.
2. Serhan, C. N., (1994) *Biochimica et Biophysica Acta* 1212, 1-25.
3. Serhan, C. N., Oliw, E., (2001) *J Clin Invest* 107, 1481-9.
4. Serhan, C. N., Maddox, J. F., Petasis, N., A, P., Brady, H. R., Colgan, S. P., Madara, J. L., (1995) *Biochemistry (USA)* 34, 14609-14615.
5. Clish, C. B., O'Brien, J. A., Gronert, K., Stahl, G. L., Petasis, N. A., Serhan, C. N., (1999) *Proc Natl Acad Sci USA* 96, 8247-52.
6. Claria, J., Lee, M. H., Serhan, C. N., (1996) *Mol. Med.* 2, 583-596.
7. Elsbach, P., Weiss, J., (1998) *Curr Opin Immunol* 10, 45-9.
8. Ganz, T., Weiss, J., (1997) *Semin Hematol* 34, 343-54.
9. Levy, O., (2000) *Antimicrob Agents Chemother* 44, 2925-31.
10. Levy, O., (2000) *Blood* 96, 2664-72.
11. Beamer, L. J., Carroll, S. F., Eisenberg, D., (1997) *Science* 276, 1861-4.
12. Dharmsathaphorn, K., Madara, J. L., (1990) *Methods Enzymol.* 192, 354-89.
13. Madianos, P. N., Papapanou, P. N., Sandros, J., (1997) *Infect. Immun.* 65, 3983-3990.
14. Lennon, P. F., Taylor, C. T., Stahl, G. L., Colgan, S. P., (1998) *J Exp Med* 188, 1433-43.
15. Dickson, M. A., Hahn, W. C., Ino, Y., Ronfard, V., Wu, J. Y., Weinberg, R. A., Louis, D. N., Li, F. P., Rheinwald, J. G., (2000) *Mol Cell Biol* 20, 1436-47.
16. Lockhart, D. J., Dong, H., Byrne, M. C., Follettie, M. T., Gallo, M. V., Chee, M. S., Mittmann, M., Wang, C., Kobayashi, M., Horton, H., Brown, E. L., (1996) *Nat Biotechnol* 14, 1675-80.
17. Taylor, C. T., Fueki, N., Agah, A., Hershberg, R. M., Colgan, S. P., (1999) *J. Biol. Chem.* 274, 19447-19450.
18. Parkos, C. A., Colgan, S. P., Liang, A., Nusrat, A., Bacarra, A. E., Carnes, D. K., Madara, J. L., (1996) *J. Cell Biol.* 132, 437-450.
19. Bevilacqua, M. P., Pober, J. S., Mendrick, D. L., Cotran, R. S., Gimbrone, M. A., (1987) *Proc. Natl. Acad. Sci.* 84, 9238-42.
20. Dittel, B. N., Wayner, E. A., McCarthy, J. B., LeBien, T. W., (1993) *Blood* 81, 2272-2282.
21. Weinrauch, Y., Foreman., A., Shu, C., Zarember, K., Levy, O., Elsbach, P., Weiss, J., (1995) *J. Clin. Invest.* 95, 1916-1924.
22. McCormick, B. A., Colgan, S. P., Delp-Archer, C., Miller, S. I., Madara, J. L., (1993) *J. Cell Biol.* 123, 895-907.
23. Colgan, S. P., Blancquaert, M. A., Thrall, M. A., Bruyninckx, M. A., (1992) *Vet. Immunol. Immunopathol.* 31, 205-227.
24. Colgan, S. P., Serhan, C. N., Parkos, C. A., Delp-Archer, C., Madara, J. L., (1993) *J. Clin. Invest.* 92, 75-82.
25. Weersink, A. J., van Kessel, K. P., van den Tol, M. E., van Strijp, J. A., Torensma, R., Verhoef, J., Elsbach, P., Weiss, J., (1993) *J Immunol* 150, 253-63.
26. Weiss, J., Elsbach, P., Olsson, I., Odeberg, H., (1978) *J Biol Chem* 253, 2664-72.
27. Gottadi, C. J., Caplan, M. J., (1992) *J. Tiss. Cult. Meth.* 14, 173-180.
28. Pugin, J., Schurer-Maly, C. C., Leturcq, D., Moriarity, A., Ulevitch, R. L., Tobias, P. S., (1993) *Proc. Nat. Acad. Sci. (USA)* 90, 2744-2748.
29. Cotran, R. S., Mayadas-Norton, T., (1998) *Pathol Biol* 46, 164-70.
30. Ouellette, A. J., (1999) *Am J Physiol* 277, G257-61.
31. Harwig, S. S., Tan, L., Qu, X. D., Cho, Y., Eisenhauer, P. B., Lehrer, R. I., (1995) *J Clin Invest* 95, 603-10.
32. Imler, J. L., Hoffmann, J. A., (2001) *Trends Cell Biol* 11, 304-11.
33. Cario, E., Podolsky, D. K., (2000) *Infect Immun* 68, 7010-7.

34. Raud, J., Palmertz, U., Dahlen, S.-E., Hedqvist, P., in *Cell-Cell Interactions in the Release of Inflammatory Mediators* P. Y.-K. Wong, C. N. Serhan, Eds. (Plenum Press, New York, 1991) pp. 185-192.
35. Levy, B. D., Clish, C. B., Schmidt, B., Gronert, K., Serhan, C. N., (2001) *Nat Immunol* 2, 612-9.
36. Pouliot, M., Clish, C. B., Petasis, N. A., Van Dyke, T. E., Serhan, C. N., (2000) *Biochemistry* 39, 4761-8.
37. Dubois, R. N., Abramson, S. B., Crofford, L., Gupta, R. A., Simon, L. S., Van De Putte, L. B., Lipsky, P. E., (1998) *Faseb J* 12, 1063-73.
38. Nisengard, R. J., Newman, M. G., Zambon, J. J., in *Oral Microbiology and Immunology* R. J. Nisengard, M. G. Newman, Eds. (W.B. Saunders, Philadelphia, 1994), vol. 2, pp. 360-384.
39. Sartor, R. B., in *Inflammatory Bowel Disease* J. B. Kirsner, R. J. Shorter, Eds. (Williams and Wilkins, Baltimore, 1995) pp. 96-124.
40. Monajemi, H., Meenan, J., Lamping, R., Obradov, D. O., Radema, S. A., Trown, P. W., Tytgat, G. N., Van Deventer, S. J., (1996) *Gastroenterology* 110, 733-9.
41. Haapamaki, M. M., Haggblom, J. O., Gronroos, J. M., Pekkala, E., Alanen, K., Nevalainen, T. J., (1999) *Hepatogastroenterology* 46, 2273-7.
42. Stoffel, M. P., Csernok, E., Herzberg, C., Johnson, T., Carroll, S. F., Gross, W. L., (1996) *Clin Exp Immunol* 104, 54-9.
43. Levin, M., Quint, P. A., Goldstein, B., Barton, P., Bradley, J. S., Shemie, S. D., Yeh, T., Kim, S. S., Cafaro, D. P., Scannon, P. J., Giroir, B. P., (2000) *Lancet* 356, 961-7.
44. Levy, O., Elsbach, P., (2001) *Curr. Infect. Dis. Reports* 3, 407-412.

One having ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

---

What is claimed is:

1. A method to treat sepsis in a subject, comprising the step of administering to a subject infected with sepsis a therapeutically effective amount of a lipoxin analog according to formula I or II, wherein formula I is:

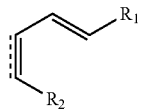

wherein $R_1$ if present can be

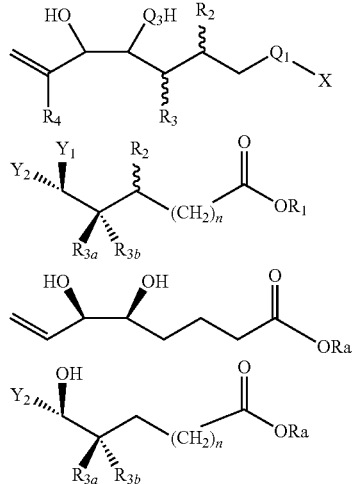

and $R_2$ if present can be

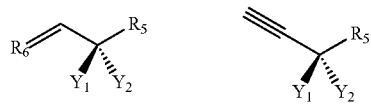

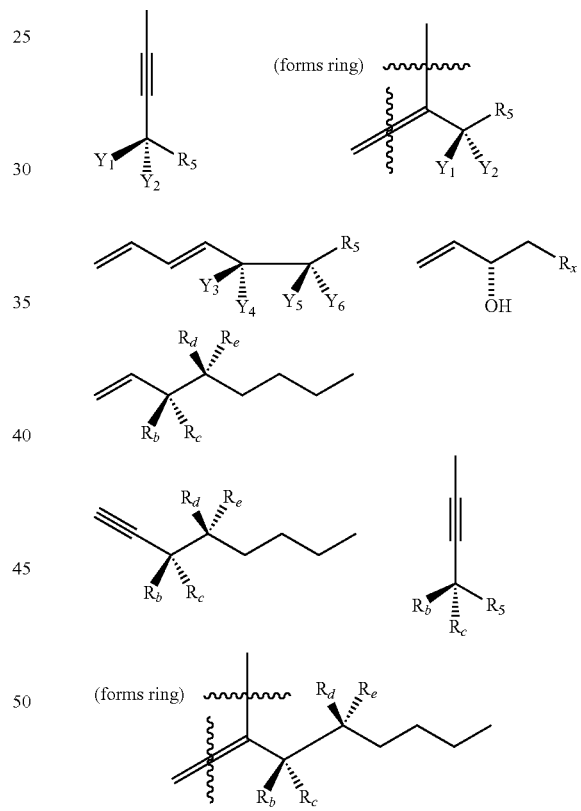

wherein X is $R_1$, $OR_1$, or $SR_1$;

wherein $R_1$ is (i) a hydrogen atom;

(ii) an alkyl of 1 to 8 carbons atoms, inclusive, which can be straight chain or branched;

(iii) a cycloalkyl of 3 to 10 carbon atoms, inclusive;

(iv) an aralkyl of 7 to 12 carbon atoms;

(v) phenyl;

(vi) substituted phenyl

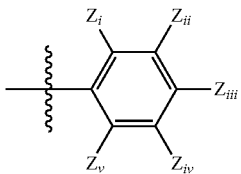

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_3$, wherein $R_x$ is 1 to 8 carbon atoms, inclusive, which can be a straight chain or branched, and hydroxyl;

(vii) a detectable label molecule; or (viii) a straight or branched chain alkenyl of 2 to 8 carbon atoms, inclusive;

wherein $Q_1$ is (C=O), $SO_2$ or (CN);

wherein $Q_3$ is O, S or NH;

wherein one of $R_2$ and $R_3$ is a hydrogen atom and the other is (a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein $R_4$ is (a) a hydrogen atom;

(b) an alkyl of 1 to 6 carbon atoms, inclusive, which can be straight chain or branched;

wherein $Y_1$ or $Y_2$ is —OH, methyl, or —SH and wherein the other is (a) a hydrogen atom (b) $CH_aZ_b$ where a+b=3, a=0 to 3, b=0 to 3; and each Z, independently, is a cyano, a nitro, or a halogen atom;

(c) an alkyl of 2 to 4 carbon atoms, inclusive, straight chain or branched; or (d) an alkoxy of 1 to 4 carbon atoms, inclusive;

or $Y_1$ and $Y_2$ taken together are (a) =NH; or (b) =O;

wherein $R_5$ is (a) an alkyl of 1 to 9 carbon atoms which can be straight chain or branched;

(b) —$(CH_2)_n$—$R_i$ wherein n=0 to 4 and $R_i$ is (i) a cycloalkyl of 3 to 10 carbon atoms, inclusive;

(ii) a phenyl; or (iii) substituted phenyl

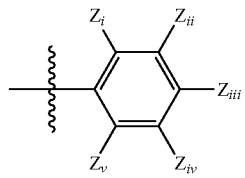

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;

(c) $R_aQ_aR_b$ wherein $Q_a$ is O or S;

wherein $R_a$ is alkylene of 0 to 6 carbons atoms, inclusive, which can be straight chain or branched;

wherein $R_b$ is alkyl of 0 to 8 carbon atoms, inclusive, which can be straight chain or branched;

(d) —C($R_{iii}$)($R_{iv}$)—$R_i$ wherein $R_{iii}$ and $R_{iv}$ are each, independently:

(i) a hydrogen atom;

(ii) $CH_aZ_b$ where a+b=3, a=0 to 3, b=0+3, and wherein each Z, independently, is a cyano, a nitro, or a halogen atom;

(e) a haloalkyl of 1 to 8 carbon atoms, inclusive, and 1 to 6 halogen atoms, inclusive, straight chain or branched; and wherein $R_6$ is (a) a hydrogen atom;

(b) an alkyl from 1 to 4 carbon atoms, inclusive, straight chain or branched;

(c) a halogen;

wherein $R_{3a}$, and $R_{3b}$ are each independently:

(a) a hydrogen atom;

(b) an alkyl of 1 to 8 carbon atoms, inclusive, which can be straight chain or branched;

(c) a cycloalkyl of 3 to 6 carbon atoms, inclusive;

(d) an alkenyl of 2 to 8 carbon atoms, inclusive, which can be straight chain or branched; or (e) $R_aQ_2R_b$ wherein $Q_2$ is —O— or —S—;

wherein $R_a$ is alkylene of 0 to 6 carbons atoms, inclusive, which can be straight chain or branched; and wherein $R_b$ is alkyl of 0 to 8 carbon atoms, inclusive, which can be straight chain or branched;

wherein $Y_3$ or $Y_4$ is —OH, methyl, hydrogen, or —SH and wherein the other is (a) a hydrogen atom;

(b) $CH_aZ_b$ wherein a+b=3, a=0 to 3, b=0 to 3, and wherein each Z, independently, is a cyano, a nitro, or a halogen atom;

(c) an alkyl of 2 to 4 carbon atoms, inclusive, straight chain or branched;

(d) an alkoxy of 1 to 4 carbon atoms, inclusive, straight chain or branched;

or $Y_3$ and $Y_4$ taken together are (a) =NH; or (b) =O;

wherein $Y_5$ or $Y_6$ is —OH, methyl, hydrogen, or —SH and wherein the other is (a) a hydrogen atom;

(b) $CH_aZ_b$ where a+b=3, a=0 to 3, b=0 to 3
wherein each Z, independently, is a cyano, a nitro, or a halogen atom;
(c) an alkyl of 2 to 4 carbon atoms, inclusive, straight chain or branched;
(d) an alkoxy of 1 to 4 carbon atoms, inclusive, straight chain or branched;
or $Y_5$ and $Y_6$ taken together are
(a) =NH; or
(b) =O;
wherein $R_a$ is
(a) a hydrogen atom; or
(b) alkyl of 1 to 8 carbon atoms;
wherein $R_x$ is
(a) substituted phenyl

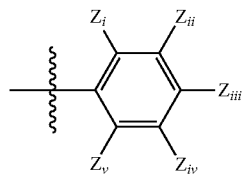

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which can be a straight chain or branched, and hydroxyl;
(b) a substituted phenoxy

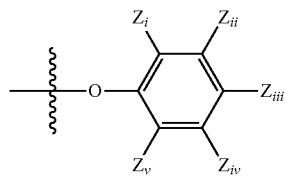

wherein $Z_i$ through $Z_v$ are as defined above; or

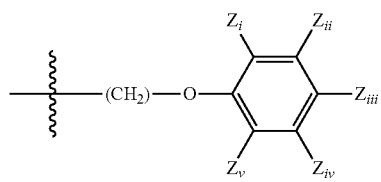

wherein $Z_i$ through $Z_v$ are as defined above.
wherein $R_b$ and $R_c$ are each independently:
(a) a hydrogen atom;
(b) a hydroxyl, or a thiol;
(c) a methyl or a halomethyl;
(d) a halogen;
(e) an alkoxy of 1 to 3 carbon atoms;
wherein $R_d$ and $R_e$ are each independently:
(a) a hydrogen atom;
(b) a hydroxyl, or thiol;
(c) a methyl or halomethyl;
(d) a halogen;
(e) an alkoxy of 1 to 3 carbon atoms; or
(f) an alkyl or haloalkyl of 2 to 4 carbon atoms, inclusive, which can be straight chain or branched; and wherein formula II is:

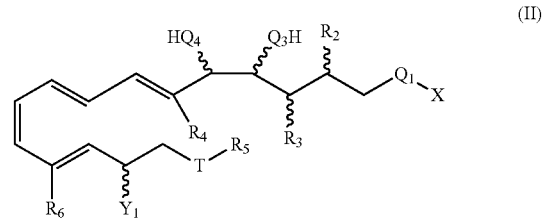

(II)

wherein X is $R_1$ $OR_1$ or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

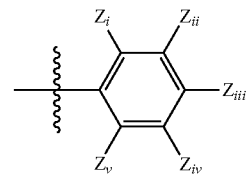

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;

wherein $R_5$ is

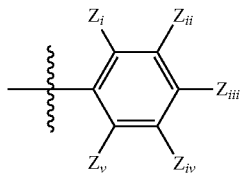

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof, such that the subject with sepsis is treated.

2. The method of claim 1, wherein the lipoxin analog has the formula:

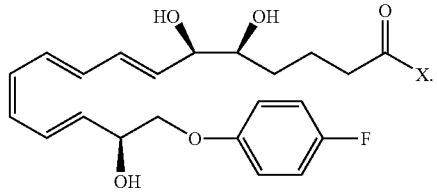

3. The method of claim 1, further comprising a pharmaceutically acceptable carrier.

4. The method of claim 2, further comprising a pharmaceutically acceptable carrier, wherein said pharmaceutically acceptable carrier is not a ketone.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: primer

<400> SEQUENCE: 1
gcacctgttc ctgatggg                                    18

<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2
agcacaaatg gaaatttctt g                                21

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
cacagtcacc tatggcaacg                                  20

<210> SEQ ID NO 4
<211> LENGTH: 19
<212> TYPE: DNA
<213> ORGANISM: Artificial sequence
<220> FEATURE:
<223> OTHER INFORMATION: primer

<400> SEQUENCE: 4
ttcttgatct tccgctggc                                   19

<210> SEQ ID NO 5

```
<211> LENGTH: 30
<212> TYPE: DNA
<213> ORGANISM: Artificial sequence
<220> FEATURE:
<223> OTHER INFORMATION: primer

<400> SEQUENCE: 5
tgacggggtc acccacactg tgcccatcta                              30

<210> SEQ ID NO 6
<211> LENGTH: 30
<212> TYPE: DNA
<213> ORGANISM: Artificial sequence
<220> FEATURE:
<223> OTHER INFORMATION: primer

<400> SEQUENCE: 6
ctagaagcat ttgcggtgga cgatggaggg                              30
```